(12) United States Patent
Ward

(10) Patent No.: US 11,795,501 B2
(45) Date of Patent: *Oct. 24, 2023

(54) METHODS FOR NEXT GENERATION GENOME WALKING AND RELATED COMPOSITIONS AND KITS

(71) Applicant: SIGMA-ALDRICH CO. LLC, St. Louis, MO (US)

(72) Inventor: Brian Ward, St. Louis, MO (US)

(73) Assignee: Sigma-Aldrich Co. LLC

( * ) Notice: Subject to any disclaimer, the term of this patent is extended or adjusted under 35 U.S.C. 154(b) by 275 days.

This patent is subject to a terminal disclaimer.

(21) Appl. No.: 17/208,538

(22) Filed: Mar. 22, 2021

(65) Prior Publication Data

US 2021/0207207 A1 Jul. 8, 2021

Related U.S. Application Data

(62) Division of application No. 15/575,711, filed as application No. PCT/US2016/033506 on May 20, 2016, now Pat. No. 10,988,802.

(Continued)

(51) Int. Cl.
*C12P 19/34* (2006.01)
*C12Q 1/6855* (2018.01)
(Continued)

(52) U.S. Cl.
CPC ............. *C12Q 1/6855* (2013.01); *C12Q 1/68* (2013.01); *C40B 20/04* (2013.01); *C12Q 2600/156* (2013.01); *C12Q 2600/16* (2013.01)

(58) Field of Classification Search
CPC .................................................. C12Q 1/6869
See application file for complete search history.

(56) References Cited

U.S. PATENT DOCUMENTS 7,972,828 B2  7/2011 Ward et al.
2012/0171727 A1  7/2012 Sohn et al.
(Continued)

FOREIGN PATENT DOCUMENTS

CN  103748236 A  4/2014
JP  2013-511285 A  4/2013
(Continued)

OTHER PUBLICATIONS

"GenomeWalker TM Kits User Manual", Clontech Laboratories, Inc., Apr. 25, 2007, pp. 1-27.
(Continued)

*Primary Examiner* — Kenneth R Horlick
(74) *Attorney, Agent, or Firm* — Sigma-Aldrich Co. LLC; Benjamin J. Sodey

(57) ABSTRACT

Methods are provided herein for identifying rare and/or unknown DNA sequences by next-generation sequencing approaches. Isolated double-stranded (ds), single-stranded (ss), or ds/ss DNA is fragmented and the fragments are polished, phosphorylated, and tailed, as necessary. Fragmentation can be enzymatic or mechanical. A universal adapter sequence is ligated to each fragment, wherein the adapter can have a top strand without a 5' phosphate, a 3' with an —H in place of the —OH, and/or a 3' extra base complementary to any base added to the polished fragments. The ligatamers may then serve as templates for amplification using a forward primer complementary to the adapter sequence and a reverse primer targeted to the fragment sequence. Compositions produced by these methods and kits adapted for performing these methods are also described herein.

10 Claims, 5 Drawing Sheets

Specification includes a Sequence Listing.

Related U.S. Application Data

(60) Provisional application No. 62/165,627, filed on May 22, 2015.

(51) Int. Cl.
    *C12Q 1/68*      (2018.01)
    *C40B 20/04*      (2006.01)

(56) References Cited

U.S. PATENT DOCUMENTS

| | | |
|---|---|---|
| 2012/0238738 A1 | 9/2012 | Hendrickson |
| 2015/0044687 A1 | 2/2015 | Schmitt et al. |
| 2015/0119255 A1 | 4/2015 | Fodor et al. |
| 2015/0265995 A1 | 9/2015 | Head et al. |

FOREIGN PATENT DOCUMENTS

| | | |
|---|---|---|
| WO | 2011/063403 A1 | 5/2011 |
| WO | 2012/041857 A1 | 4/2012 |
| WO | 2013/096839 A1 | 6/2013 |
| WO | 2013/142389 A1 | 9/2013 |
| WO | 2013/177220 A1 | 11/2013 |
| WO | 2016/191272 A1 | 12/2016 |

OTHER PUBLICATIONS

International Search Report received for PCT Patent Application No. PCT/US2016/033506 dated Sep. 22, 2016, 6 pages.
Arnold et al., "Vectorette PCR: A Novel Approach to Genomic Walking", PCR Methods and Applications, 1991, pp. 39-42.
Fu et al., "Molecular indexing enables quantitative targeted RNA sequencing and reveals poor efficiencies in standard library preparations", PNAS vol. 111 No. 5, Feb. 4, 2014, pp. 1891-1896.
Padegimas et al., "Adaptor Ligation-Based Polymerase Chain Reaction-Mediated Walking", Analytical Biochemistry, vol. 260, 1998, 149-153 pages.
Schmitt et al., "Detection of ultra-rare mutations by next-generation sequencing", PNAS, vol. 109, No. 36, Sep. 4, 2012, pp. 14508-14513.
Xu et al., "Randomly broken fragment PCR with 5'end-directed adaptor for genome walking", Scientific Reports, vol. 3, Dec. 10, 2013, pp. 1-7.
Communication pursuant to Article 94(3) EPC received for European Patent Application No. 16800544.5 dated Apr. 6, 2022, 3 Pages.

```
                        SEQUENCE LISTING

<160> NUMBER OF SEQ ID NOS: 137

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acactctttc cctacacgac gctcttccga tct                                   33

<210> SEQ ID NO 2
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 2
gatcggaaga                                                                10

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatcggaaga g                                                              11

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatcggaaga gc                                                             12

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatcggaaga gch                                                            13

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatcggaaga gd                                                             12

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatcggaaga h                                                              11

<210> SEQ ID NO 8
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 8 gatcggaagb                                                          10

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gatcggaaga gchv                                                     14

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatcggaaga gdh                                                      13

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gatcggaaga hd                                                       12

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gatcggaagb h                                                        11

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 gatcggaahb                                                          10

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (14)..(14)
<223> OTHER INFORMATION: a, c, t, or g
<220> FEATURE:
<223> OTHER INFORMATION: See specification as filed for detailed
      description of substitutions and preferred embodiments

<400> SEQUENCE: 14
gatcggaaga gchn                                                      14

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a, c, t, or g
<220> FEATURE:
<223> OTHER INFORMATION: See specification as filed for detailed
      description of substitutions and preferred embodiments

<400> SEQUENCE: 15
gatcggaaga gdn                                                       13

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, or g
<220> FEATURE:
<223> OTHER INFORMATION: See specification as filed for detailed
      description of substitutions and preferred embodiments

<400> SEQUENCE: 16
gatcggaaga hn                                                        12

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: a, c, t, or g
<220> FEATURE:
<223> OTHER INFORMATION: See specification as filed for detailed
      description of substitutions and preferred embodiments

<400> SEQUENCE: 17
gatcggaagb n                                                         11

<210> SEQ ID NO 18
<211> LENGTH: 10
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, or g
<220> FEATURE:
<223> OTHER INFORMATION: See specification as filed for detailed
      description of substitutions and preferred embodiments

<400> SEQUENCE: 18 gatcggaahn                                                                 10

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (33)..(40)
<223> OTHER INFORMATION: a, c, t, or g

<400> SEQUENCE: 19
acactctttc cctacacgac gctcttccga tcnnnnnnnn t                              41

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 20
nnnnnnnnga tcggaagagc                                                     20

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 21
nnnnnnnnga tcggaagag                                                      19

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 22
nnnnnnnnga tcggaaga                                                        18

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 23
nnnnnnnnga tcggaag                                                         17

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 24
nnnnnnnnga tcgaa                                                           16

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 25
nnnnnnnnga tcggaagagc h                                                    21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 26
nnnnnnnnga tcggaagagd                                                       20

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 27
nnnnnnnnga tcggaagah                                                        19

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 28
nnnnnnnnga tcggaagb                                                         18

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 29
nnnnnnnnga tcggaah                                                          17

<210> SEQ ID NO 30
<211> LENGTH: 22
<212> TYPE: DNA
<213> ORGANISM: Artificial Sequence
<220> FEATURE:
```

<223> OTHER INFORMATION: Description of Artificial Sequence: Synthetic
    oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
    description of substitutions and preferred embodiments

<400> SEQUENCE: 30
nnnnnnnnga tcggaagagc hv                                              22

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
    description of substitutions and preferred embodiments

<400> SEQUENCE: 31
nnnnnnnnga tcggaagagd h                                               21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
    description of substitutions and preferred embodiments

<400> SEQUENCE: 32
nnnnnnnnga tcggaagahd                                                 20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
    description of substitutions and preferred embodiments

<400> SEQUENCE: 33
nnnnnnnnga tcggaagbh                                                  19

<210> SEQ ID NO 34
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 34
nnnnnnnnga tcggaahb                                                        18

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (22)..(22)
<223> OTHER INFORMATION: a, c, t, or g
<220> FEATURE:
<223> OTHER INFORMATION: See specification as filed for detailed
      description of substitutions and preferred embodiments

<400> SEQUENCE: 35
nnnnnnnnga tcggaagagc hn                                                   22

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (21)..(21)
<223> OTHER INFORMATION: a, c, t, or g
<220> FEATURE:
<223> OTHER INFORMATION: See specification as filed for detailed
      description of substitutions and preferred embodiments

<400> SEQUENCE: 36
nnnnnnnnga tcggaagagd n                                                    21

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (20)..(20)
<223> OTHER INFORMATION: a, c, t, or g
```

-continued

```
<220> FEATURE:
<223> OTHER INFORMATION: See specification as filed for detailed
      description of substitutions and preferred embodiments

<400> SEQUENCE: 37
nnnnnnnnga tcggaagahn                                                    20

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (19)..(19)
<223> OTHER INFORMATION: a, c, t, or g
<220> FEATURE:
<223> OTHER INFORMATION: See specification as filed for detailed
      description of substitutions and preferred embodiments

<400> SEQUENCE: 38
nnnnnnnnga tcggaagbn                                                     19

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (18)..(18)
<223> OTHER INFORMATION: a, c, t, or g
<220> FEATURE:
<223> OTHER INFORMATION: See specification as filed for detailed
      description of substitutions and preferred embodiments

<400> SEQUENCE: 39
nnnnnnnnga tcggaahn                                                      18

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccatctcatc cctgcgtgtc tccgactcag                                         30

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
```
ctgagtcgga gacacg                                                          16

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctgagtcgga gacac                                                           15

<210> SEQ ID NO 43
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctgagtcgga gaca                                                            14

<210> SEQ ID NO 44
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctgagtcgga gac                                                             13

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctgagtcgga ga                                                              12

<210> SEQ ID NO 46
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctgagtcgga g                                                               11

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

-continued ctgagtcgga                                        10

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ctgagtcgga gacacgd                                17

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ctgagtcgga gacach                                 16

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctgagtcgga gacad                                  15

<210> SEQ ID NO 51
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctgagtcgga gacb                                   14

<210> SEQ ID NO 52
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctgagtcgga gad                                    13

<210> SEQ ID NO 53
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ctgagtcgga gb                                     12

<210> SEQ ID NO 54
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctgagtcgga h                                                          11

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55 ctgagtcggb                                                            10

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctgagtcgga gacacgdb                                                   18

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ctgagtcgga gacachd                                                    17

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ctgagtcgga gacadh                                                     16

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctgagtcgga gacbd                                                      15

-continued

```
<210> SEQ ID NO 60
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ctgagtcgga gadb                                                         14

<210> SEQ ID NO 61
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctgagtcgga gbd                                                          13

<210> SEQ ID NO 62
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ctgagtcgga hb                                                           12

<210> SEQ ID NO 63
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctgagtcggb h                                                            11

<210> SEQ ID NO 64
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64 ctgagtcghb                                                              10

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: a, c, t, or g
<220> FEATURE:
<223> OTHER INFORMATION: See specification as filed for detailed
``` description of substitutions and preferred embodiments

<400> SEQUENCE: 65
ctgagtcgga gacacgdn                                          18

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: a, c, t, or g
<220> FEATURE:
<223> OTHER INFORMATION: See specification as filed for detailed
      description of substitutions and preferred embodiments

<400> SEQUENCE: 66
ctgagtcgga gacachn                                           17

<210> SEQ ID NO 67
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a, c, t, or g
<220> FEATURE:
<223> OTHER INFORMATION: See specification as filed for detailed
      description of substitutions and preferred embodiments

<400> SEQUENCE: 67
ctgagtcgga gacadn                                            16

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: a, c, t, or g
<220> FEATURE:
<223> OTHER INFORMATION: See specification as filed for detailed
      description of substitutions and preferred embodiments

<400> SEQUENCE: 68
ctgagtcgga gacbn                                             15

<210> SEQ ID NO 69
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t, or g
<220> FEATURE:

```
<223> OTHER INFORMATION: See specification as filed for detailed
      description of substitutions and preferred embodiments

<400> SEQUENCE: 69
ctgagtcgga gadn                                                         14

<210> SEQ ID NO 70
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: a, c, t, or g
<220> FEATURE:
<223> OTHER INFORMATION: See specification as filed for detailed
      description of substitutions and preferred embodiments

<400> SEQUENCE: 70
ctgagtcgga gbn                                                          13

<210> SEQ ID NO 71
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: a, c, t, or g
<220> FEATURE:
<223> OTHER INFORMATION: See specification as filed for detailed
      description of substitutions and preferred embodiments

<400> SEQUENCE: 71
ctgagtcgga hn                                                           12

<210> SEQ ID NO 72
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: a, c, t, or g
<220> FEATURE:
<223> OTHER INFORMATION: See specification as filed for detailed
      description of substitutions and preferred embodiments

<400> SEQUENCE: 72
ctgagtcggb n                                                            11

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, or g
```

```
<220> FEATURE:
<223> OTHER INFORMATION: See specification as filed for detailed
      description of substitutions and preferred embodiments

<400> SEQUENCE: 73 ctgagtcghn                                                                10

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ccatctcatc cctgcgtgtc tccgactcag t                                        31

<210> SEQ ID NO 75
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(38)
<223> OTHER INFORMATION: a, c, t, or g

<400> SEQUENCE: 75
ccatctcatc cctgcgtgtc tccgactcag nnnnnnnn                                 38

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 76
nnnnnnnnct gagtcggaga cacg                                                24

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 77
nnnnnnnnct gagtcggaga cac                                                 23
```

```
<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 78
nnnnnnnnct gagtcggaga ca                                            22

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 79
nnnnnnnnct gagtcggaga c                                             21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 80
nnnnnnnnct gagtcggaga                                               20

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 81
nnnnnnnnct gagtcggag                                                19
```

```
<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 82
nnnnnnnnct gagtcgga                                                      18

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 83
nnnnnnnnct gagtcgg                                                       17

<210> SEQ ID NO 84
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 84
nnnnnnnnct gagtcg                                                        16

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 85
nnnnnnnnct gagtcggaga cacgd                                              25
```

```
<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 86
nnnnnnnnct gagtcggaga cach                                              24

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 87
nnnnnnnnct gagtcggaga cad                                               23

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 88
nnnnnnnnct gagtcggaga cb                                                22

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 89
```

-continued nnnnnnnnct gagtcggaga d                              21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 90
nnnnnnnnct gagtcggagb                                20

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 91
nnnnnnnnct gagtcggah                                 19

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 92
nnnnnnnnct gagtcggb                                  18

<210> SEQ ID NO 93
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 93
nnnnnnnnct gagtcgh                                                    17

<210> SEQ ID NO 94
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 94
nnnnnnnnct gagtcggaga cacgdb                                          26

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 95
nnnnnnnnct gagtcggaga cachd                                           25

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 96
nnnnnnnnct gagtcggaga cadh                                            24

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 97
nnnnnnnnct gagtcggaga cbd                                            23

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 98
nnnnnnnnct gagtcggaga db                                             22

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 99
nnnnnnnnct gagtcggagb d                                              21

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 100
nnnnnnnnct gagtcggahb                                                20

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 101
nnnnnnnnct gagtcggbh                                              19

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<223> OTHER INFORMATION: See specification as filed for detailed
      description of substitutions and preferred embodiments

<400> SEQUENCE: 102
nnnnnnnnct gagtcghb                                               18

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (26)..(26)
<223> OTHER INFORMATION: a, c, t, or g
<220> FEATURE:
<223> OTHER INFORMATION: See specification as filed for detailed
      description of substitutions and preferred embodiments

<400> SEQUENCE: 103
nnnnnnnnct gagtcggaga cacgdn                                      26

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (25)..(25)
<223> OTHER INFORMATION: a, c, t, or g
<220> FEATURE:
<223> OTHER INFORMATION: See specification as filed for detailed
      description of substitutions and preferred embodiments

<400> SEQUENCE: 104
nnnnnnnnct gagtcggaga cachn                                       25

<210> SEQ ID NO 105
<211> LENGTH: 24
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (24)..(24)
<223> OTHER INFORMATION: a, c, t, or g
<220> FEATURE:
<223> OTHER INFORMATION: See specification as filed for detailed
      description of substitutions and preferred embodiments

<400> SEQUENCE: 105
nnnnnnnnct gagtcggaga cadn                                            24

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (23)..(23)
<223> OTHER INFORMATION: a, c, t, or g
<220> FEATURE:
<223> OTHER INFORMATION: See specification as filed for detailed
      description of substitutions and preferred embodiments

<400> SEQUENCE: 106
nnnnnnnnct gagtcggaga cbn                                             23

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (22)..(22)
<223> OTHER INFORMATION: a, c, t, or g
<220> FEATURE:
<223> OTHER INFORMATION: See specification as filed for detailed
      description of substitutions and preferred embodiments

<400> SEQUENCE: 107
nnnnnnnnct gagtcggaga dn                                              22

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:

-continued

```
<221> NAME/KEY: modified_base
<222> LOCATION: (21)..(21)
<223> OTHER INFORMATION: a, c, t, or g
<220> FEATURE:
<223> OTHER INFORMATION: See specification as filed for detailed
      description of substitutions and preferred embodiments

<400> SEQUENCE: 108
nnnnnnnnct gagtcggagb n                                              21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (20)..(20)
<223> OTHER INFORMATION: a, c, t, or g
<220> FEATURE:
<223> OTHER INFORMATION: See specification as filed for detailed
      description of substitutions and preferred embodiments

<400> SEQUENCE: 109
nnnnnnnnct gagtcggahn                                                20

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (19)..(19)
<223> OTHER INFORMATION: a, c, t, or g
<220> FEATURE:
<223> OTHER INFORMATION: See specification as filed for detailed
      description of substitutions and preferred embodiments

<400> SEQUENCE: 110
nnnnnnnnct gagtcggbn                                                 19

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, or g
<220> FEATURE:
<221> NAME/KEY: modified_base
<222> LOCATION: (18)..(18)
<223> OTHER INFORMATION: a, c, t, or g
<220> FEATURE:
<223> OTHER INFORMATION: See specification as filed for detailed
      description of substitutions and preferred embodiments
```

```
<400> SEQUENCE: 111
nnnnnnnnct gagtcghn                                                    18

<210> SEQ ID NO 112
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(38)
<223> OTHER INFORMATION: a, c, t, or g

<400> SEQUENCE: 112
ccatctcatc cctgcgtgtc tccgactcag nnnnnnnnt                              39

<210> SEQ ID NO 113
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acactctttc cctacacgac gctcttccga tc                                     32

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
acactctttc cctacacgac gctc                                              24

<210> SEQ ID NO 115
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
agtaaaaata ggtgattttg gtcta                                             25

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ccactgtccc tagatacttc ca                                                22

<210> SEQ ID NO 117
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 117
gcctccagac ttaaagatgg                                              20

<210> SEQ ID NO 118
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
acgctgcgga ggc                                                     13

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ttccgcaccc agcag                                                   15

<210> SEQ ID NO 120
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
cacctccacc gtgca                                                   15

<210> SEQ ID NO 121
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ggggaccagg ggc                                                     13

<210> SEQ ID NO 122
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gtcaaggcac tcttgcc                                                 17

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 123
gacatgatga gatcttcctg tat                                      23

<210> SEQ ID NO 124
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
aagtcacttc attaaattaa gaagagtt                                 28

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ccgagcttag cagctagg                                            18

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ggaatatttc tcattcccag atta                                     24

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gcgccacaaa gagacatt                                            18

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
atagaaaatc tttctcctgc tca                                      23

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129 cattttttgtt gtccagcc                                                                18

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gcctttcctg cagcc                                                                    15

<210> SEQ ID NO 131
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
atgttaatga tcttttttctt tatttaaaa                                                    29

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cttgaacatc ccctcagac                                                                19

<210> SEQ ID NO 133
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ggcccagcgt cca                                                                      13

<210> SEQ ID NO 134
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gttgagaacc agccctg                                                                  17

<210> SEQ ID NO 135
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 135
ccttggggca gacca                                                      15

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ggacatttat ttgtaccttc tgtaat                                          26

<210> SEQ ID NO 137
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
cacccaggta gttgcg                                                     16
```

METHODS FOR NEXT GENERATION GENOME WALKING AND RELATED COMPOSITIONS AND KITS

CROSS-REFERENCE TO RELATED APPLICATIONS

The present application is a divisional of U.S. application Ser. No. 15/575,711, now U.S. Pat. No. 10,988,802. U.S. application Ser. No. 15/575,711 was filed Nov. 20, 2017, under 35 U.S.C. 371, as a National Stage application of PCT International Application Serial No. PCT/US2016/033506, filed May 20, 2016, which claims priority to U.S. Provisional Application Ser. No. 62/165,627, filed May 22, 2015. Each of the foregoing applications are incorporated herein by reference in their entirety.

SEQUENCE LISTING

The present application contains a Sequence Listing which has been filed electronically in ASCII format and is hereby incorporated by reference in its entirety. Said ASCII copy, created on Mar. 19, 2021, is named SIG219_US-PCD1_SL.txt and is 46,761 bytes in size.

FIELD

The present disclosure describes methods and kits for sequencing a nucleic acid, and more particularly, for next generation sequencing. Compositions created by the methods described herein are also disclosed.

BACKGROUND

This section provides background information related to the present disclosure which is not necessarily prior art.

Genome walking is a useful method of identifying and amplifying specific as-yet unknown DNA sequences based on knowledge of nearby sequences. See, e.g., Arnold & Hodgson (1991) *PCR Methods & Apps.* 1:39-42.

Xu et al. (2013) *Sci. Reports* 3:3465 report that the basic techniques of genome walking can be made more specific, efficient, and reproducible by modifying these techniques to include genomic fragmentation, followed by capping the fragments with a 5' adapter to allow for semi-nested polymerase chain reaction (PCR) of the fragments.

Next-generation sequencing can identify rare mutations from out of a larger pool of sequences. Schmitt et al. (2012) *Proc. Natl. Acad. Sci. USA* 109:14508-13.

When using next-generation sequencing approaches, it is necessary to employ some sort of indexing scheme to be able to discern between mutations that were present in the starting template and mutations that are introduced by imperfect copying during the replication process. Fu et al. (2014) *Proc. Natl. Acad. Sci. USA* 111:1891-96. For example, by barcoding the starting template material, it is possible to determine which low-frequency mutations were present in the original sample, and which were introduced as copying errors during the amplification process.

SUMMARY

This section provides a general summary of the disclosure, and is not a comprehensive disclosure of its full scope or all of its features.

In general terms, the methods and kits described herein reduce the total number of primers necessary to sequence a given number of nucleotides, making it possible to analyze a larger number of sequences in a given reaction, thus enabling a finer degree of sequence specificity. In other words, the methods and kits described herein could be used to detect low-frequency sequences in a larger population of related sequences with a more precise resolution than was possible with prior art sequencing methods and tools. These methods and kits can be used to create compositions as described herein.

In an embodiment, the present disclosure provides a composition comprising a plurality of polynucleotides each comprising a native sequence and a universal adapter sequence. The native sequence comprises a sequence of interest and a native sequence priming domain, and the universal adapter sequence comprises from 5' to 3' an adapter priming domain and, optionally, a barcode domain consisting of 1 to 20 nucleotides, and wherein the universal adapter sequence is located a fixed distance from the 5' end of the sequence of interest.

In another embodiment, there is provided a method for copying a sequence of interest. The method comprises amplifying a plurality of template polynucleotides that each comprise a native sequence and a universal adapter sequence on at least one end, wherein the native sequence comprises the sequence of interest, and the universal adapter sequence comprises from 5' to 3' an adapter priming domain and, optionally, a barcode domain consisting of 1 to 20 nucleotides, wherein the universal adapter sequence is located a fixed distance from the 5' end of the sequence of interest, such that the nucleotide sequence between the universal adapter sequence and the sequence of interest defines an identification sequence that is unique to a given template and its progeny amplicons, and wherein the amplification is primed with a pair of primers comprising a universal primer that is identical to at least 10 bp of the adapter priming domain of the universal adapter sequence and a first reverse primer that is complementary to a region of the native sequence downstream of the sequence of interest.

In yet another embodiment, there is provided a kit comprising a DNA polymerase, a DNA ligase, and a plurality of universal adapter polynucleotides, wherein each universal adapter polynucleotide comprises a 3' modification on the reverse strand to make the 3' end non-extendible, and each universal adapter polynucleotide comprises a priming sequence common to all universal adapter polynucleotides and, optionally, a barcode domain consisting of 1 to 20 nucleotides.

BRIEF DESCRIPTION OF THE DRAWINGS

The drawings described herein are for illustrative purposes only of selected embodiments and not all possible implementations, and are not intended to limit the scope of the present disclosure.

DEFINITIONS

Figure 1:
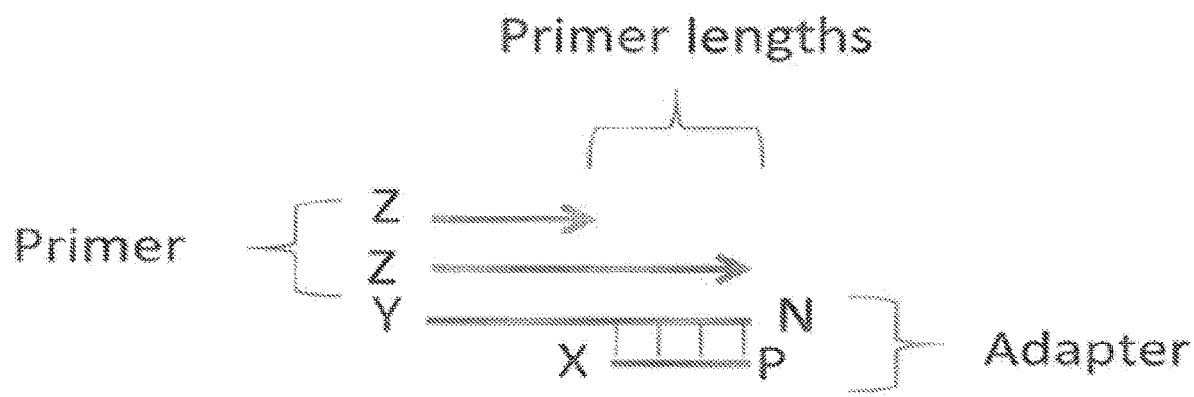
FIG. 1 shows structures for an exemplary universal adapter sequence and two exemplary primers for use in the methods described herein.

The terms "barcode domain" or "barcode sequence" refers to a unique sequence that is not present in the native sequence or template polynucleotide and which is used for molecular identification.

As used herein, "identification sequence" refers to the sequence between the universal adapter sequence at the upstream end of a polynucleotide and the sequence of interest. In embodiments in which the universal adapter sequence includes a barcode domain, the identification sequence also includes the barcode domain and, thus, can be termed a "barcode identification sequence." The identification sequence, which may include the barcode domain, provides molecular identification.

A "priming domain" or "priming sequence" refers to a nucleotide sequence having a free 3' end onto which complementary nucleotide(s) can be added.

As used herein, "sequence of interest" means a sequence that is analyzed and/or examined in a given sequencing procedure. Any sequence can define or contain a sequence of interest. Non-limiting examples of sequences of interest include a single nucleotide polymorphism (SNP), an insertion or deletion mutation (INDEL), a multiple tandem repeat (MTR), a polynucleic polymorphism, a ribosomal RNA sequence, a homeobox domain sequence, a tRNA sequence, or other suchlike. A sequence of interest can be a single base, or a string of bases. Where the sequence of interest comprise more than one base, the distance between the barcode domain and the sequence of interest can be measured from any base within the sequence of interest, so long as it is measured the same way for all identification sequences.

The terms "upstream" and "downstream" refer to positions defined in terms relative to the forward strand of a double stranded (ds) DNA molecule. Sequences "upstream" are found at positions nearer the 5' end of the forward strand (and therefore nearer the 3' end of the reverse strand) than are "downstream" sequences, which are nearer the 3' end of the forward strand (and therefore also nearer the 5' end of the reverse strand).

As used herein, the term "universal adapter" refers to a polynucleotide comprising a priming domain, wherein the priming domain is common to many or all universal adapter molecules in a given reaction. In certain embodiments, the universal adapter may also include a barcode domain that can vary among different universal adapter molecules.

As used herein, the terms "complementary" or "complementarity" refer to the formation of double-stranded nucleic acids by base pairing through specific hydrogen bonds. The base paring may be standard Watson-Crick base pairing (e.g., A pairs with T and G pairs with C). The base pairing also may be Hoogsteen or reversed Hoogsteen hydrogen bonding. Complementarity between two nucleic acids may be partial and expressed as a percentage (e.g., about 65%, 70%, 75%, 80%, 85%, 90%, 95%, etc.), if only some of the base pairs have perfectly matched complementary. Complementarity may also be complete (i.e., 100%), if all the base pairs of the two nucleic acids are perfectly matched (i.e., % A=% T, % G=% C).

A degenerate sequence comprises of at least one degenerate nucleotide. A degenerate nucleotide is a nucleotide that can perform the same function or yield the same output as a structurally different nucleotide. A degenerate nucleotide can have 2-fold degeneracy (i.e., it can be one of two nucleotides), 3-fold degeneracy (i.e., it can be one of three nucleotides), or 4-fold degeneracy (i.e., it can be one of four nucleotides. A or C or G or T). Nucleotides having 3-fold degeneracy include "B" (can be C or G or T), "D" (can be A or G or T), "H" (can be A or C or T), and "V" (can be A or C or G). Nucleotides having 2-fold degeneracy include "K" (can be G or T), "M" (can be A or C), "R" (can be A or G), "Y" (can be C or T), "S" (can be C or G), and "W" (can be A or T).

DETAILED DESCRIPTION

The methods, kits, and compositions described herein are useful for analyzing nucleic acids of any type and from any source, such as animal, plant, bacteria, virus, fungus, or synthetically made. For example, target nucleic acids may be naturally occurring DNA or RNA, recombinant molecules, genomic DNA (gDNA) or cDNA. Further, target nucleic acids may be a specific portion of a genome of a cell, such as an intron, regulatory region, allele, variant, or mutation. Template nucleotides for use in methods as described herein may be assembled from a whole genome or any portion of a genome, as well as from a mixture of multiple genomes. In certain embodiments, the template polynucleotides can be assembled from an environmental isolate; non-limiting examples of environmental samples include a soil sample, a sample from a body of water such as a pond or estuary, a sewage sample, a surface swab, such as from a hospital, etc. In some embodiments, the target nucleic acids may be mRNA, tRNA, rRNA, ribozymes, antisense RNA, or siRNA. The template nucleotides may be of any length, such as at least about 25, 50, 100, 500, 1000, 2500, 5000, 10000 bp, greater than 10000 bp, or an intact chromosome.

The methods, kits, and compositions described herein possess many advantages relative to prior art technologies. For example, the methods described herein combine the advantage of Arnold & Hodgson's (1991) "vectorette"-style amplification strategy (universal primer template synthesis after specific primer elongation) with next generation sequencing adapter/ligation strategies.

Moreover, the methods described herein make it possible to digest rather than purify away interfering adapter sequences. This advantage is particularly salient for applications involving molecular barcoding, because if they are not removed, excess barcoded adapters can act as primers during amplification, thus destroying the very benefit sought from the use of barcodes. For this reason it is necessary to remove the barcoded adapters prior to amplification. While purification using beads or columns is common in the art, these strategies run the risk of losing extremely rare sequences from the sample. In addition, such purification steps are either difficult or cumbersome for automated workflows, typically requiring extensive human intervention in the process and complicating high-throughput robotic work schemes. The methods, kits, and compositions described herein make possible an enzymatic digest that targets only unligated adapter without loss of valuable template molecules, thus facilitating automation.

Compositions described herein can optionally include an identification sequence composed of the combination of an optional adapter barcode sequence, which is located a landmark distance from a sequence of interest, and the (landmark) sequence between the barcode domain sequence and the sequence of interest. The landmark distance can range from 1 nucleotide to several hundred nucleotides, for example from 1-50 nucleotides, from about 50-100 nucleotides, from about 100-200 nucleotides, or from about 200-500 nucleotides. The unique molecular identification sequence formed from this combination of barcode sequence and landmark sequence makes it possible to achieve any given number of unique identification sequences from a set of substantively shorter barcodes with equivalent molecular identification. For example 100 bp fragments with 8 degenerate base adapters require 11 or 12 degenerate bases ignoring the landmark distance. In other embodiments, the compositions described comprise an identification sequence that is composed of the landmark sequence. The length and the sequence of nucleotides comprising the landmark sequence provide the unique molecular identification.

Although it is routine in the art to perform exponential amplification within a given tube, followed by linear amplification in the same tube to generate single stranded amplicons, the methods described herein can also include—in certain embodiments—linear amplification in a single tube followed by exponential amplification in the same tube. In this way, multiple direct template copies can be generated prior to copies of exponential amplification leading to greater confidence that identically barcoded sequence descended from the same parent molecule.

Polymerase Chain Reaction Methods

Methods for amplifying a sequence of interest by PCR are described herein, in which a plurality of native fragment polynucleotides are appended to a plurality of universal adapter polynucleotides. Each universal adapter comprises an adapter priming domain common to all universal adapter polynucleotides and optionally a barcode domain comprising a given sequence and number of nucleotides, e.g. 1-20 nucleotides. The barcode domain generally is degenerate (i.e., comprises at least one degenerate nucleotide). The barcode domain conveys information that can be used to identify a series of amplicons as being descended from a given template molecule. As the universal adapter is appended to its native fragment molecule, the barcode domain, when present, will be located at a given distance (i.e., landmark distance) from a sequence of interest within the native fragment. The distance can range from one nucleotide to several hundred nucleotides. The nucleotide sequence spanning the distance from the adaptor (or barcode of the adaptor) to the sequence of interest can be termed a landmark sequence. The combination of barcode domain and the length and sequence of the landmark sequence defines an identification sequence that has a greater than 90% probability—for example, greater than 91%, greater than 92%, greater than 93%, greater than 94%, greater than 95%, greater than 96%, greater than 97%, greater than 98%, greater than 99% or greater than 99.9%—of being molecularly unique within the amplification reaction. Therefore, all amplicons in the reaction that bear a given identification sequence can be reliably understood to have descended from a common template that acquired the identification sequence based on the original attachment event that placed an adapter or a given barcode domain within the adapter at a given distance from the sequence of interest within the native fragment. The templates are then amplified using a pair of primers that includes at least one primer that is complementary to the adapter priming sequence of the universal adapter.

Figure 2:
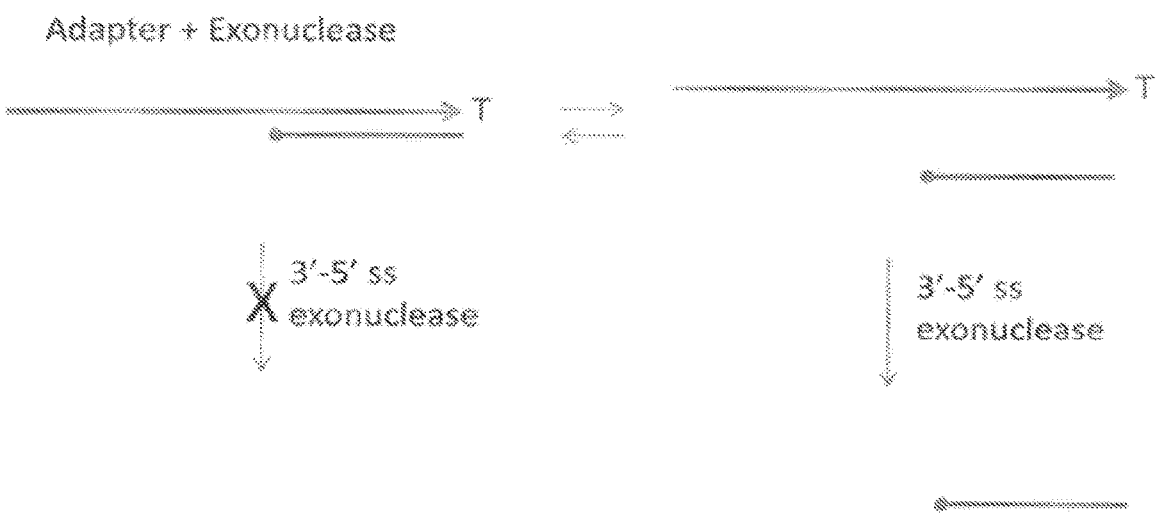
FIG. 2 shows a mechanism by which unattached excess universal adapter sequence can be removed from a system prior to amplification by digestion with a 3' to 5' single-strand specific exonuclease. In the drawing, "T" represents thymidine. This nuclease treatment step obviates the need to purify excess universal adapter molecules out of the system.
Figure 2:
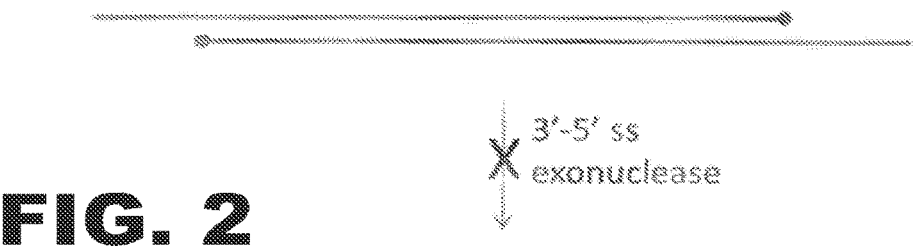
Figure 3:
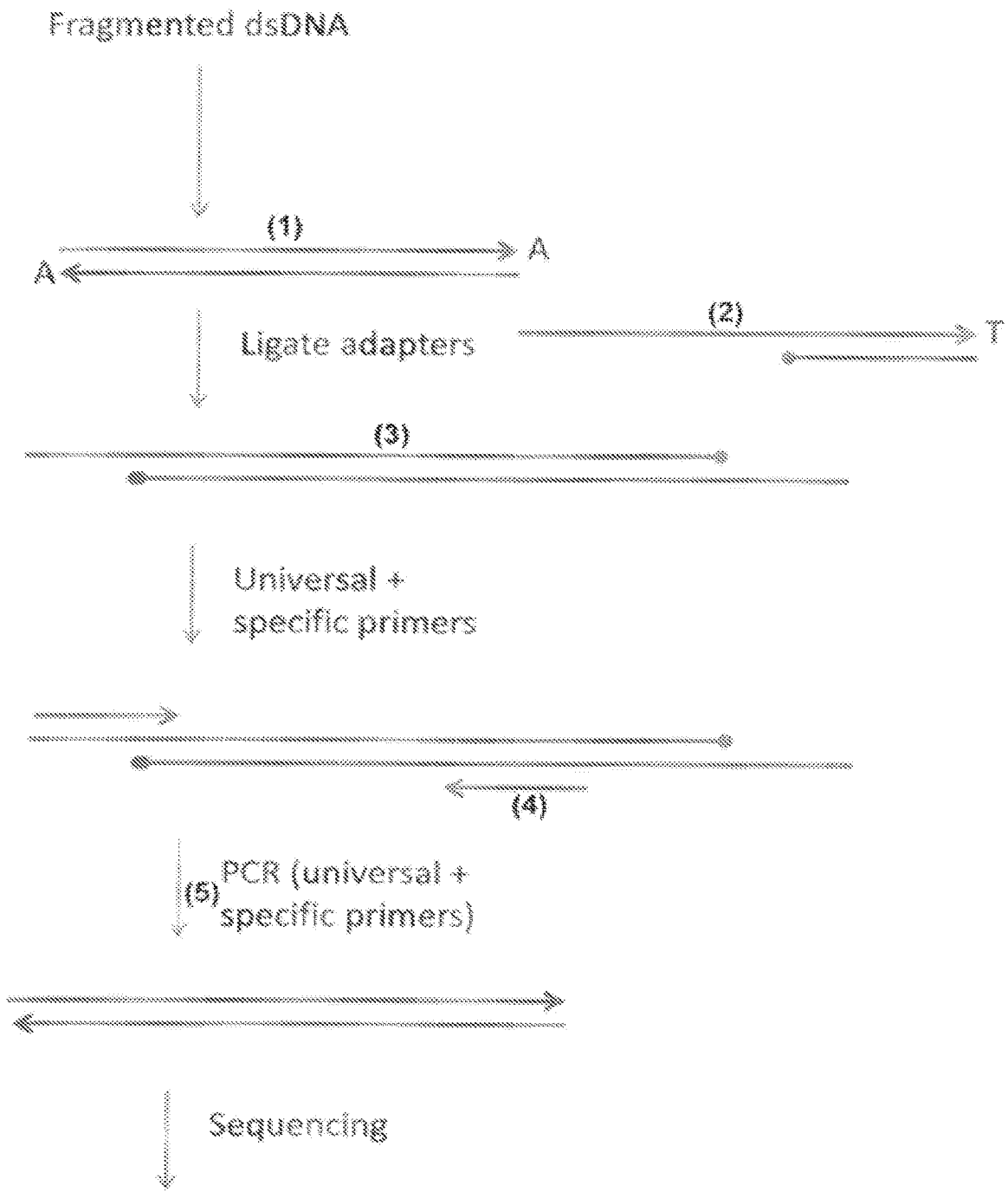
FIG. 3 illustrates the workflow of an exemplary method described herein.

For example, FIGS. 2 and 3 illustrate the work-flow of a sample embodiment of the methods described herein. As shown in FIG. 2, when the two strands of the unligated universal adapter are held together by complementary base pairing, the double-stranded structure is resistant to digestion by ExoI, whose nuclease activity is specific to ssDNA. However, once the two strands of the adapter are melted apart, the top strand becomes susceptible to ExoI digestion because its 3' end is accessible. Even after melting, the bottom strand of the universal adapter in FIG. 2 may remain insusceptible to ExoI digestion because its 3' end modification. Meanwhile, the universal adapters that have been connected to native fragments (ligatamers) are insusceptible to ExoI digestion, because the ligation of universal adapters to duplex DNA results in stable duplex adapter-template ligatamers. Therefore, using adapters whose melting temperature allows at least some of the adapter oligonucleotides to dissociate provides a convenient method to remove adapter using a 3'-5' single strand specific exonuclease (e.g., ExoI) from the template pool before amplification, to reduce non-specific amplification of unligated universal adapter molecules.

Turning next to FIG. 3, one can see the native fragments (1) are ligated to the universal adapters (2), creating template molecules (3) with 3' end blocks. Following digestion with a 3' to 5' single-strand specific exonuclease (not shown) to remove unligated universal adapter molecules, primer extension of a primer (4) specific to a sequence within the native fragment sequence can generate double-stranded templates that include the sequence of interest, which can then be amplified (5) for sequencing and further analysis. The double-stranded templates generated via PCR using universal primers proceeds after the specific primer extension. Phosphorylated specific primers could facilitate ligation of NGS reverse adapters.

A method as described herein can be carried out with various structures of primer pairs. In some embodiments, the primer pair includes a reverse primer complementary to a sequence downstream of the sequence of interest. In other embodiments, amplification involves a plurality of primer pairs, in each of which the forward primer is complementary to the priming sequence of the universal adapter, while the plurality of reverse primers are each complementary to a sequence downstream of one or more positions of interest within one or more native fragments.

The present disclosure also provides a method comprising more than one set of amplification steps, in which a first set of steps involve one set of primers, and a subsequent set or sets of steps involve additional reverse primers, each of which is complementary to a region upstream of the reverse primer from an earlier amplification, but still downstream of the sequence of interest. In certain embodiments, the reverse primer (or plurality of reverse primers) in one of the subsequent amplification steps carries (or each carry) a 5' sequencing tag. In certain embodiments, the melting temperature of the reverse primer used in the earlier amplification steps is greater than the melting temperature of the forward primer, for example, at least about 2° C., at least about 5° C., at least about 7° C., at least about 10° C., at least about 12° C., or at least about 15° C.

The universal adapter sequence can be attached to the native fragment by any of well known methods in the art. For example, in certain embodiments the universal adapter is attached to the native fragment by ligation using a ligase.

In other embodiments, the universal adapter sequence is appended to the native fragment by primer extension.

The universal adapters used in the methods herein can be designed in various manners. In certain embodiments the universal adapters include a 5' forward strand overhang, optionally in which the 3' end of the reverse strand is modified to be non-extendible, for example with a hydrogen in place of the hydroxyl, with an acetate or phosphate group, or with an unpaired nucleotide(s). In certain embodiments, the universal adapters are blunt ended, for example the 3' end for the forward strand. In other embodiments, the universal adapters have at least one unpaired base on the 3' end of the forward strand or the 5' end of the reverse strand. In certain embodiments, the 5' end of the forward strand is modified to be unligatable, for example with a hydroxyl in place of the phosphate.

The sequence of interest can be a nucleotide or a string of nucleotides of a native fragment polynucleotide. In certain embodiments the sequence of interest sits within or is a mutation. In certain embodiments the sequence of interest sits within or is a single nucleotide polymorphism (SNP). In certain embodiments the sequence of interest sits within or is an insertion or deletion (INDEL).

The methods above can further comprise removing unligated universal adapter polynucleotides from the system before amplification, for example by digesting with a 3' to 5' single-strand specific exonuclease, such as ExoI. In certain embodiments, the amplification employs a "vectorette" style genome-walking procedure, similar to the process described in Arnold & Hodgson (1991).

The native fragments that can be used in the methods are not limited to any particular sources or any particular preparations. In certain embodiments, the native fragments come from fragmented genomic DNA, for example DNA fragmented by enzymatic digestion or by physical shearing methods such as sonication and cavetation. In other embodiments, the native fragments are cDNA generated from all or part of the transcriptome(s) of an organism or organisms.

Likewise, the adapter priming sequence can be selected from various sequences known in the art. In certain embodiments, the adapter priming sequence is selected from the group contained in Table 4.

By way of non-limiting example, a PCR method as described herein may include ligating a plurality of universal adapter sequences to a plurality of native sequence polynucleotides. Additionally or alternatively, the method may include extending the first reverse primer and forming a forward strand complementary to the primer extension product including the adapter sequence. Additionally or alternatively, the method may include treating the ligation products with a 3' to 5' single-strand specific exonuclease prior to amplifying. In certain embodiments the exonuclease treatment may occur before primer extension, while in other embodiments primer extension occurs before exonuclease treatment. Additionally or alternatively, the method may include amplifying the amplicons with a pair of primers comprising the universal primer and a second reverse primer that is complementary to a sequence upstream of the region complementary to the first reverse primer.

In certain embodiments, at least one adapter polynucleotide for use in the methods described herein is hydroxylated at a 5' end and/or modified at a 3' end with a modification selected from the group consisting of hydrogen, phosphate, acetate, or one or more unpaired nucleotides.

In certain embodiments, the second reverse primer comprises a 5' sequencing tag.

In certain embodiments, the template polynucleotides comprise fragmented genomic DNA. In other embodiments, the template polynucleotides comprise cDNA.

In certain embodiment, the melting temperature of the first reverse primer is higher than the melting temperature of the universal primer, e.g., at least about 2° C., at least about 5° C., at least about 7° C., at least about 10° C., at least about 12° C., or at least about 15° C.

In a particular embodiment, there is provided a method for amplifying a sequence of interest as follows: a blood sample is extracted from a patient and all gDNA is isolated and purified from the sample. The isolated and purified gDNA is digested with a selection of endonucleases and the fragments are end-polished by blunt ending the fragments and then adding a single adenosine overhang at each of the 3' ends of the fragments. A plurality of universal adapter molecules is added to the fragment mixture, along with T4 DNA ligase and ATP. After a suitable interval of time the ligation digested with ExoI exonuclease. The exonuclease is then heat deactivated (e.g., 80° C. for 20 minutes, 95° C. for 2 minutes). A thermostable DNA polymerase and a plurality of primers are added to the mixture. One of these primers is complementary to the priming sequence on the universal adapter molecule, while the others are each complementary to a known sequence downstream of a sequence of interest. The primers complementary to known downstream sequences all have melting temperatures of about 65° C., while the primer complementary to the adapter sequence has a melting temperature of 60° C. After ten rounds of annealing at 65° C. and extension at 72° C., another ten rounds of amplification are run with annealing at 60° C. Another set of reverse primers are then added that work as "nested" primer relative to the first set of reverse primers. These nested primers can have melting temperatures between 60° C. and 65° C. The next primers include sequencing tags on their 5' ends. Another 10-20 rounds of amplification are performed with annealing at 60° C., followed by sequencing of the amplification products. Relative prevalence of different molecular species in the initial (pre-amplification) template pool can be inferred based on the number of unique identification sequences associated with each sequence of interest variant.

Nucleotide Compositions

The present disclosure also provides compositions produced with the methods described herein. These compositions comprise a plurality of amplicon polynucleotides, each comprising a native sequence and a universal adapter sequence, wherein the native sequence comprises a sequence of interest and a native sequence priming domain, and the universal adapter sequence comprises an adaptor priming domain and, optionally, a barcode domain consisting of 1 to 20 nucleotides. The universal adapter sequence is located a fixed distance from the 5' end of the sequence of interest, such that the nucleotide sequence between the universal adapter sequence and the sequence of interest together define an identification sequence. In embodiments, in which the universal adapter sequence includes the barcode domain, the identification sequence also includes the barcode domain (see FIG. 6).

Figure 6:
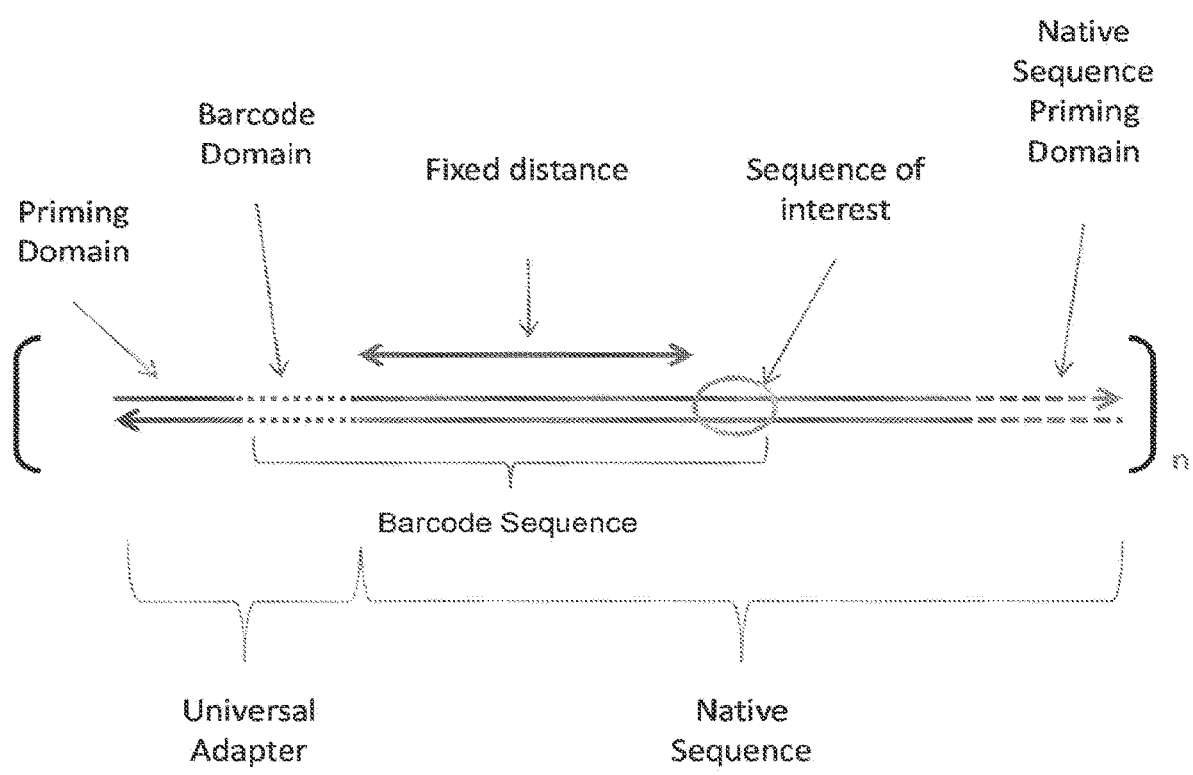
FIG. 6 shows an embodiment of the unique amplicon components.

As represented in FIG. 6, these compositions comprise a plurality of amplicon polynucleotides, each of which is descended from an original template molecule that was created when a universal adapter polynucleotide was appended to a native fragment comprising a sequence of interest. Once the various amplicon sets within the composition have been sequenced, the identification sequence of each amplicon set will be determined by the user, who will then be able to compute-based on the number of distinct identification sequences associated with each sequence of interest—the relative prevalence of different sequence arrangements at each of a variety of positions of interest within a given genome and/or transcriptome.

In certain embodiments, the individual amplicons have two ends that are each different from the other. For example, in certain embodiments the 10 nucleotides at the 5' end of the forward strand and the 10 nucleotides at the 3' end of the forward strand of each amplicon have no more than 90% identity, for example no more than 85% identity, no more than 80% identity, no more than 75% identity, no more than 70% identity, no more than 65% identity, no more than 60% identity, or no more than 50% identity. In certain embodiments, the probability that a given set of amplicons that all share an identification sequence derived from the same original template molecule is greater than 90%—for example, greater than 91%, greater than 92%, greater than 93%, greater than 94%, greater than 95%, greater than 96%, greater than 97%, greater than 98%, greater than 99%, or greater than 99.9%.

The compositions described herein can contain one or more unextended primers. In certain embodiments, these primers include one or more of a primer complementary to the priming sequence of the universal adapters and a primer complementary to a region of a native fragment located downstream of the sequence of interest.

In certain embodiments, the composition does not comprise a substantial amount of universal adapter sequence that is not appended to a native fragment molecule. In certain embodiments, the composition does not comprise any universal adapter sequence that is not appended to a native fragment molecule.

In certain embodiments, the composition comprises at least two reverse primer sequences that are complementary to different portions of the same native fragment sequence, optionally in which at least one of these two reverse primers have melting temperatures that are at least about 2° C., at least about 5° C., at least about 7° C., at least about 10° C., at least about 12° C., or at least about 15° C. greater than the melting temperature of the forward primer.

By way of non-limiting example, a composition as described herein may comprise a universal primer whose nucleotide sequence is complementary to the adapter priming domain and/or a primer whose nucleotide sequence is complementary to a region of the native sequence. A priming domain means a nucleotide sequence to which a primer hybridizes or a nucleotide sequence which is identical to a supplied primer.

At least one polynucleotide in the composition may be hydroxylated at a 5' end, and/or modified at a 3' end with a modification selected from the group consisting of hydrogen, phosphate, acetate, and an unpaired nucleotide.

The amplification product can be the result of amplification between a universal sequence and native sequence. In other embodiments, the amplification product can be the result of amplification between 5' and 3' universal adapter sequences.

In certain embodiments, the product of degenerate molecular possibilities and potential distance of the sequence of interest exceeds the number of ligation events.

Once the native fragments have been conjoined to the universal adapters, the probability that a given template molecule will be identical to another template merely by chance is given by $1 \div [F/(X^n \times L)]$ where F is the number of starting native sequence fragments, X is the number of degenerate nucleotides at each position of the barcode domain, n is the number of degenerate nucleotide positions of the barcode domain and L is length of the starting native sequence fragments. Therefore, in other words, if two molecules in the composition share an identification sequence, it is highly unlikely that they are descended from different template molecules.

In certain embodiments, the length of starting native sequence fragments is highly uniform. In other embodiments, the lengths of starting native sequence fragments are variegated. When the lengths are variegated, the variegation can result from post DNA isolation fragmentation, e.g., enzymatic fragmentation or mechanical fragmentation. Template molecules within the composition can, in certain embodiments, result from ligation of universal adapter sequences to randomly fragmented DNA.

Kits

Kits for performing the methods described above are also disclosed herein. Kits as described herein may contain some or all of the components necessary for performing the methods described above. For example, kits as described herein may contain one or more of the following: primers; universal adapter molecules; ligase; 3' to 5' single-strand specific exonuclease, such as ExoI; DNA polymerase; reverse transcriptase; ligase buffer; PCR buffer; dNTPs; $MgCl_2$; nuclease free tubes and pipette tips; and restriction endonucleases with corresponding reaction buffers.

By way of non-limiting example, a kit as described herein may comprise a DNA polymerase, a DNA ligase, and a plurality of universal adapter polynucleotides, wherein each universal adapter polynucleotide comprises a 3' modification on the reverse strand to make the 3' end non-extendible, and wherein each universal adapter polynucleotide comprises a priming sequence common to all universal adapter polynucleotides, and, optionally, a barcode domain consisting of 1 to 20 nucleotides. The barcode domain can be degenerate.

The kit can further comprise various optional components as needed for performing the methods described herein, and a person having ordinary skill can determine such necessary components. Non-limiting examples of such components include: a 3' to 5' single-strand specific exonuclease, a nuclease-free polymerase buffer, a nuclease-free ligase buffer, a universal primer complementary to at least 10 bp of the priming sequence and any combination thereof.

The 3' modification can be any known modification that can prevent polymerase extensions. In certain embodiments, the 3' modification is selected from the group consisting of hydrogen, phosphate, acetate, and an unpaired nucleotide. Additionally or alternatively, each universal adapter may be blunt on at least one end. Additionally or alternatively, the adapter polynucleotide may be partially double-stranded and partially single-stranded, wherein the forward strand comprises an unpaired overhang at the 5' end. Additionally or alternatively, the forward strand of the adapter polynucleotide may comprise a 3' end suitable for ligation to prepared native sequences. Additionally or alternatively, the forward strand of the universal adapter polynucleotide may comprise a 3' end complementary to the 3' end of the native sequences. Additionally or alternatively, the forward strand of the universal adapter polynucleotide may comprise a 5' end complementary to the 5' end of the native sequences. Additionally or alternatively, the forward and reverse strands of the adapter polynucleotide may comprise at least one blunt end. For example, the reverse strand of the universal adapter polynucleotide comprises a 5' phosphate.

In certain embodiments, the kit comprises a universal primer that is identical in sequence to at least a portion of the adapter polynucleotide that is common to all adapter polynucleotides.

In certain embodiments, the kit includes a universal primer that is identical in sequence to the whole length of the portion of the adapter polynucleotide that is common to all adapter polynucleotides.

In a particular embodiment, the kit includes: a tube containing assorted universal adapter and primer molecules contained in Table 4; a tube of primer oligos complementary to the adapter molecules; T4 DNA ligase; ligase buffer with ATP; ExoI exonuclease; thermostable DNA polymerase; Klenow polymerase; dATP; dNTPs; and $MgCl_2$.

Primers

Any oligonucleotide sequence can be used as a primer in the methods, kits, and compositions described herein. Primers for use in the methods, kits, and compositions described herein may comprise from at least about 10—e.g., at least 15, at least 20, at least 25, or at least 30—to about 50 bp. Such primers may be DNA, RNA or combinations thereof. Furthermore, primers may comprise modified phosphate-sugar backbones. Primers comprise a sequence complementary to the attachment site of whatever template sequence is to be amplified. For example, primers complementary to the adapter molecules can include those contained in Table 4. Primers can be made synthetically using conventional nucleic acid synthesis technology. For example, the primers can be synthesized via standard phosphoramidite technology utilizing a nucleic acid synthesizer. Such synthesizers are available, e.g., from Applied Biosystems, Inc. (Foster City, Calif.).

If the user wishes to isolate and analyze particular amplicons within the compositions described herein, primers can be labeled, e.g., with biotin or a haptan or a fluorophore, to facilitate the subsequent capture or purification. Primers can also be labeled with a radioactive isotope, such as $H^3$ or $P^{32}$. Additionally, primers may carry a non-annealing sequence at their 5' ends, such as a so-called sequencing tag, for use in subsequent amplification or hybridization steps.

Universal Adapter Polynucleotides

Universal adapter sequences for use in the methods, kits, and compositions described herein must include at least a priming domain sequence that is common to many or all universal adapter molecules in a given reaction. In certain embodiments, the universal adapter may also include a barcode domain that can vary among different universal adapter molecules. The universal adapter sequence may comprise from 5' to 3', a universal priming domain and, optionally, a barcode domain. The barcode domain sequence generally is degenerate. In certain embodiments, the degenerate barcode domain comprises 1 to 20 degenerate nucleotides. In other embodiments, the barcode domain is not degenerate. In certain embodiments, the universal adapters are suitable for hybridization to solid support tethered primers and/or probes. In certain embodiments, the fixed universal sequence may be suitable for hybridization to capture structures.

The priming domain in the universal adapter may be a single sequence or a plurality of sequences, and can be any length. By way of non-limiting example, the priming sequence can be at least 10, at least 15, at least 20, at least 25, at least 30, at least 35, at least 40, or at least 45 bp in length. By way of non-limiting example, the priming sequence can be no more than 100, no more than 90, no more than 80, no more than 70, no more than 60, no more than 50, no more than 45, no more than 40, no more than 35, no more than 30, no more than 25, no more than 20, or no more than 15 bp in length. For example, priming sequences for use in the methods, kits, and compositions described herein can be 15 to 25 bp in length. Non-limiting examples of the priming domain sequences include those shown in Table 4.

Figure 4:
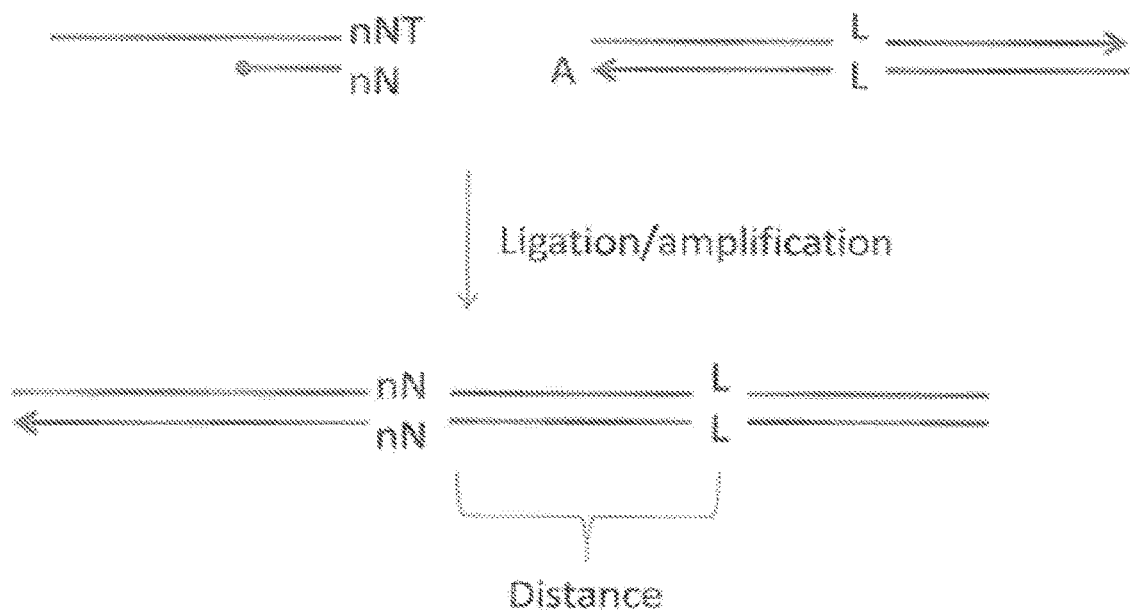
FIG. 4 illustrates the principle by which the barcode domain together with the sequence of interest define a unique identification sequence.

The barcode domain may be any number of nucleotides in length, and can be any order of nucleotides. For example, the barcode can be 1, 2, 3, 4, 5, 6, 7, 8, 9, 10, 11, 12, 13, 14, 15, 16, 17, 18, 19, or 20 nucleotides in length. The barcode sequence conveys information about the antecedent lineage of a given amplicon. Because the identity of a molecular ancestor in the compositions and methods described herein is determined by a unique identification sequence, and because the barcode is only part of the identification sequence, it is not necessary that every universal adapter sequence in a given reaction have a unique barcode. The principle by which the barcode sequence gives rise to a unique molecular identification sequence is illustrated in FIG. 4. In the context of FIG. 4, "n" signifies an integer greater than 0. For example, n can be an integer from 1 to 20. "N" signifies any nucleotide base selected from adenosine (A), guanosine (G), thymidine (T), and cytosine (C). "L" signifies a landmark, such as a SNP, at the sequence of interest. L can be any distance from nN. As a result, the combination of nN plus the sequence intervening between nN and L defines an identification sequence that has only one chance in $4^n \times D$ of being indistinct from another independently constructed identification sequence, wherein D is the number of nucleotide bases between nN and L. For example, when D is 100, the molecular uniqueness for n ranging from 1 to 12 is shown in the table below:

| n | Uniqueness |
| --- | --- |
| 1 | 400 |
| 2 | 1600 |
| 3 | 6400 |
| 4 | 25600 |
| 5 | 102400 |
| 6 | 409600 |
| 7 | 1638400 |
| 8 | 6553600 |
| 9 | 26214400 |
| 10 | 1.05E+08 |
| 11 | 4.19E+08 |
| 12 | 1.68E+09 |

Different universal adapter molecules in a given reaction can share a common priming sequence and yet have barcode domains of different lengths. The barcode domain is generally positioned downstream of the priming sequence. In some embodiments the priming sequence and the barcode domain will together account for the whole length of a universal adapter molecule, while in other embodiment a universal adapter may comprise additional sequences beyond the priming sequence and the barcode domain.

Native Fragment Polynucleotides

Template molecules for use in the methods and compositions described herein are composed of a combination of at least a universal adapter sequence and a native fragment sequence, optionally in combination with additional sequences. The native fragment polynucleotides for use in the methods and compositions described herein can derive from any source or plurality of sources. By way of non-limiting examples, the native fragments can derive from a human individual, an environmental isolate, or a crop plant. In certain embodiments, the native fragments include fragmented genomic DNA. In other embodiments, the native fragments include cDNA. Techniques to fragment DNA are well known in the art, including digestion with one or more endonucleases and mechanical means. The native fragments can be any length. For example, the native fragments can be at least 20 bp, at least 100 bp, at least 500 bp, at least 1000 bp, at least 5000 bp, or at least 10000 bp long. By way of non-limiting example, the native fragments can be no more than 100 kbp, no more than 90 kbp, no more than 80 kbp, no more than 70 kbp, no more than 60 kbp, no more than 50 kbp, no more than 40 kbp, no more than 30 kbp, no more than 20 kbp, or no more than 10 kbp long.

The native fragments can be attached to the universal adapters by any one of many methods known to those of ordinary skill in the art. For example, in some embodiments the native fragments are appended to the universal adapters by ligation with a suitable ligase. Ligases for use in such an application are well known to those of ordinary skill. Those of ordinary skill will appreciate that if ligation is intended, it may be advantageous to perform so-called "end polishing" steps of the fragmented template prior to its attachment to a universal adapter. Such end polishing may optionally include steps such as blunt-ending and/or phosphorylating and/or the addition of unpaired nucleotides to one or the other end to create so-called "sticky ends" that are complementary to the opposite end of the universal adapter sequence. In some embodiments, a universal adapter sequence may be appended to the native fragment by means of primer extension.

Single-Tube Polymerase Chain Reaction

In addition to the templates and primers described above, amplification by polymerase chain reaction will require a thermostable polymerase. Such polymerases are well known to those of skill in the art, for example a thermostable polymerase described in U.S. Pat. No. 7,972,828 to Ward et al., the entire contents of which are hereby incorporated by reference.

The individual distinct steps of the methods described herein can each be performed in a separate and distinct vessel, such as a polypropylene PCR tube. In other embodiments, more than one step can be performed in a given tube. In certain embodiments, all of the steps of the methods described herein can be performed in a single tube.

In so-called "single tube" embodiments of the methods described herein, the native fragment DNA is added to a tube along with ligase, polymerase, 3' to 5' single-strand specific exonuclease, primers, dNTPs, and all other ingredients necessary for polymerase chain reaction. In such embodiments, the ingredients may optionally include a fluorescent dye, such as N,N-dimethyl-N'-[4-[(E)-(3-methyl-1,3-benzothiazol-2-ylidene)methyl]-1-phenylquinolin-1-ium-2-yl]-N'-propyl-propane-1,3-diamine (SYBR® Green), to track the progressive formation of dsDNA amplicons. The amplification methods for use with the methods, kits, and compositions described herein can be non-quantitative, semi-quantitative, or quantitative, as necessary for a given application. Those of ordinary skill will readily understand how to optimize amplification strategies to achieve quantitative or non-quantitative results as desired.

The amplification can proceed in a series of progressive steps using nested primers. In single-tube embodiments, it may be advantageous to design the most downstream reverse primer to have a higher melting point than the forward primer. In this way, the first round or rounds of primer extension can occur at a higher—and thus more stringently specific—annealing temperature. This high temperature extension of the reverse primer may occur in either a linear or an exponential fashion. In this way, the excess universal adapters may be removed from the system prior to exponential amplification, but without the need for a purification step. Subsequent rounds of amplification may then proceed at a lower annealing temperature and in an exponential fashion. In certain embodiments, the melting temperatures of the upstream and downstream reverse primers may differ by at least about 2° C., at least about 5° C., at least about 7° C., at least about 10° C., at least about 12° C., or at least about 15° C.

Diagnostic Methods

The methods, kits, and compositions described herein can be used in the detection of mutation(s) for the diagnosis of disease. In certain embodiments, the disease occurs in a crop plant or in an animal, such as a farm animal, a pet, or a human. In particular embodiments, the methods, kits, and compositions described herein can be used to detect tumors in a human. The tumors to be detected can be of any type, such as benign tumor, pre-malignant tumor or malignant (i.e., cancerous) tumor. In particular, because of the enhanced ability of the methods, kits, and compositions described herein to detect low frequency genetic patterns amidst a background of much more prevalent genetic patterns, it is possible to detect signature genetic patterns indicative of oncogenesis at very early stages, when the cells bearing such oncogenic signature patterns constitute only a very small fraction of all cells in a given patient sample, such as a blood sample. For example, the oncogenic signature pattern may be found in only 1 out of $10^4$, 1 out of $10^6$, 1 out of $10^9$, 1 out of $10^{12}$, or 1 out of $10^{15}$ cells. Similarly, an oncogenic pattern could be measured from circulating cell free DNA.

Agricultural Applications

The methods, kits, and compositions described herein also can be used in agricultural breeding programs. For example, the methods, kits, and compositions described herein can be used to determine the ingress of a given trait following a cross-breeding.

Environmental Monitoring

The methods, kits, and compositions described herein also can be used to monitor the biome of a given environment. For example, the methods, kits, and compositions described herein can be used to determine the relative prevalence of various microorganisms in a pond, a stream, a sewer, or a reservoir. In, addition, the methods, kits, and compositions described herein can be used to monitor the relative prevalence of different microorganisms in an industrial setting, such as a fermentation vat or a brewing vessel.

EXAMPLES

Without further description, it is believed that one of ordinary skill in the art can, using the preceding description and the following illustrative examples, make and utilize the compositions described herein and practice the claimed methods. The following working examples, therefore, specifically point out representative embodiments of the present invention, some preferred, and are not to be construed as limiting in any way the remainder of the disclosure.

Example 1

An exemplary and illustrative universal adapter for use in a method, kit, or composition as described herein is shown in FIG. 1. In this illustrative example, "N" represents a cohesive base or set of cohesive bases for ligating to native fragments. The unpaired N can be used to help attach the universal adapter sequence to native fragment molecule. "P" signifies a 5' phosphate. "X" can be any non-extendible modification to the 3' end, including, e.g., mismatched bases, 3' phosphate, 3' acetate, —H in place of the 3'-OH, etc. "Y'" can be any non-ligatable modification to the 5' end, e.g., —OH in place of phosphate. "Z" can be any non-ligatable modification to the 5' end. Z can be the same as or different from Y.

Example 2

Total gDNA from a sample was digested with HpyCH4V (NEB, Ipswitch, Mass.). The fragments were end-repaired with an end-repair and A-tailing kite (e.g., KAPA® Hyper kit; Wilmington, Mass.). The result was a plurality of dA tailed gDNA Hpy fragments. These gDNA fragments were then incubated with a universal adapter polynucleotide in the presence or absence of DNA ligase, followed by polymerase chain reaction (PCR) amplification with a forward primer complementary to the universal adapter sequence and a plurality of 21 different reverse primers complementary to a variety of sequences within the gDNA.

Of the 21 primer sets, 19 resulted in amplicons with anticipated product sizes from the ligated templates. 16 of these 19 were single-product amplicons. Only 3 of the 21 primer sets gave rise to amplicon products with the non-ligated templates.

Example 3

Total gDNA from a sample was Covaris fragmented to approximately 150 bp. The fragments were end-repaired with an end-repair and A-tailing kite (e.g., KAPA® Hyper kit; Wilmington, Mass.). The result was a plurality of dA tailed gDNA fragments. These gDNA fragments were then incubated with a universal adapter polynucleotide in the presence DNA ligase, followed by polymerase chain reaction (PCR) amplification with a forward primer complementary to the universal adapter sequence and a plurality of 22 different reverse primers complementary to a variety of sequences within the gDNA.

All 22 primer sets resulted in amplicons with anticipated multiple product sizes from the ligated templates.

Example 4

A series of universal adapter molecules were prepared from the sequences shown in Table 1 by combining, denaturing and slowly cooling equimolar amounts of the top strand sequence with each of the bottom strand sequences. The duplex adapters below were incubated with or without ExoI exonuclease at 37° C. in PCR buffer. The incubated samples were then analyzed on a Bioanalyzer (Agilent Tech., Santa Clara, Calif.). The "p" on the bottom strand indicates phosphate. The top strand was successfully digested in every sample containing ExoI.

TABLE 1

| Universal adapter series | | | |
|---|---|---|---|
| Top strand sequence | | Melting temp. | SEQ ID NO: |
| 5' ACACTCTTTCCCTACACGACGCT CTTCCGATCT 3' | | | 1 |
| # | Bottom strand sequences | | |
| 1 | 3' pGGCTAGp 5' | 13° C. | — |
| 2 | 3' pAGGCTAGp 5' | 17° C. | — |
| 3 | 3' pAAGGCTAGp 5' | 17° C. | — |

TABLE 1-continued

| Universal adapter series | | | |
|---|---|---|---|
| 4 | 3' pGAAGGCTAGp 5' | 21.8° C. | — |
| 5 | 3' pAGAAGGCTAGp 5' | 27.8° C. | 2 |
| 6 | 3' pGAGAAGGCTAGp 5' | 32.4° C. | 3 |
| 7 | 3' pCGAGAAGGCTAGp 5' | 41.2° C. | 4 |

Figure 5:
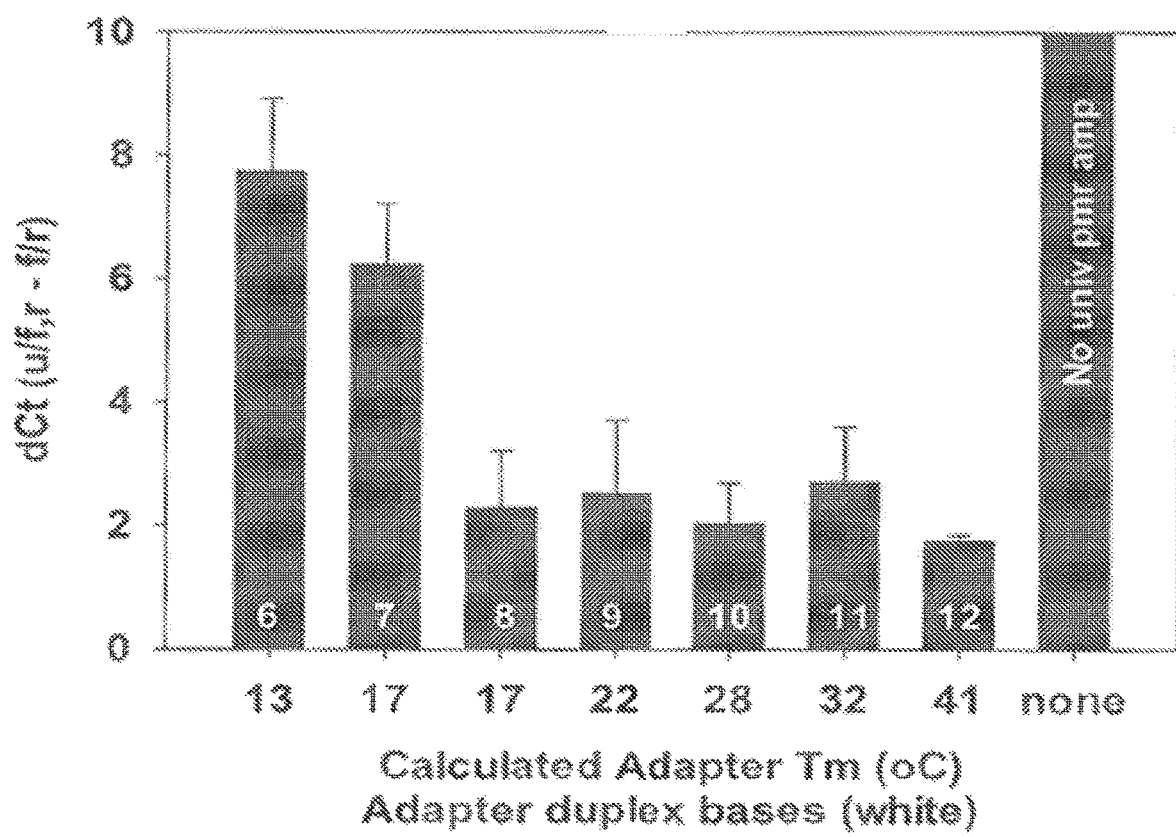
FIG. 5 shows the dCT values following ligation with the universal adapters presented in Table 2 below.

The universal adapters of Table 1 were then ligated to a template test sequence. Once again, samples of each ligatamer were incubated at 37° C. in PCR buffer with or without ExoI, followed by quantitative PCR (qPCR) amplification. PCR was done using either a forward primer specific for the universal adapter sequence, or with a forward primer specific for the test sequence. The reverse primer was specific for the test sequence in all amplification reactions. The difference between the Ct value obtained with the universal forward primer and the test sequence specific forward primer is indicative of the ligation efficiency for each universal adapter structure. FIG. 5 shows the resulting dCt values (u/f,r–f/r) from each of these reactions. As can be seen, the efficiency of ligation was essentially equal for Adapters #3-7. The dCt values were identical as between the ligatamers that were ExoI treated and the ligatamers that were not.

These data show that universal adapters with truncated bottom strands are capable of highly efficient ligation at 20° C., even when the adapter duplex lengths are as short as 7 bp. All duplex adapters were digestible at 37° C. with ExoI, while the 3' phosphate protected ligatamers were completely resistant to ExoI digestion.

Example 5

A test sequence template was amplified by qPCR under the cycling temperatures indicated in Table 2 below. A variety of forward primers specific to the universal adapter sequence were used, one for each reaction. These forward primers each had different lengths with correspondingly different melting temperatures, ranging from 54.9° C. to 68.5° C. A control reaction contained a forward primer specific to the test sequence template, with a melting temperature of 70° C. All reactions used the same reverse primer, which was specific to a sequence within the test sequence template and which had a melting temperature of 70° C. Ct values from these reactions are shown in Table 2.

TABLE 2

| qPCR (Ct) at various temperature cycles | | | |
|---|---|---|---|
| | Cycling temperatures (° C.) | | |
| F $T_m$ | 94°/72° | 94°/65°/72° | 94°/50°/72° |
| 54.9° C. | N/A | 21.69 | 11.09 |
| 57.2° C. | N/A | 16.64 | 11.47 |
| 58.2° C. | N/A | 12.71 | 11.797 |
| 63.0° C. | N/A | 12.45 | 11.63 |
| 66.4° C. | 28.13 | 11.86 | 11.06 |
| 67.0° C. | 18.93 | 12.24 | 11.42 |
| 68.5° C. | 15.88 | 12.10 | 11.31 |
| 70.0° C. | 19.72 | 10.77 | 10.65 |

As can be seen from the data in Table 2, it is clear that by pairing forward and reverse primers so that the reverse primer has a melting temperature sufficiently higher than that of the forward primer, it is possible to optimize the primer pair to enable a two-step process, in which a linear extension reaction is first run at a high temperature, followed by an exponential amplification at a lower temperature. In other words, it is possible to perform linear amplification from the native fragment to the ligated universal adapter followed by exponential amplification between the universal and native sequence primer in a reaction containing both primers.

To further test this single-tube approach, another set of qPCR reactions were run with the same primer sets used in the Table 2 procedure. This run included 20 cycles of 94° C./72° C., followed by 20 cycles of 94° C./60° C./72° C. This qPCR run gave rise to the "1$^{st}$ Ct" data shown in Table 3 below. An identical set of reaction mixtures were run in parallel for 2×20 cycles of 94° C./60° C./72° C. This run gave rise to the "2$^{nd}$ Ct" data shown in Table 3 below. The "dCt" column of Table 3 shows the difference between the 1$^{st}$ and 2$^{nd}$ Ct data for each primer pair. A dCt of approximately 3-4 would be expected for a linear first step then exponential second step in the 1$^{st}$ Ct set of reactions. Such dCt values indicates that the first 20 cycles of the "1$^{st}$ Ct" qPCR involved only linear amplification, while a large (>7) dCt value indicates that the "1$^{st}$ Ct" qPCR involved linear and exponential or exponential amplification. As can be seen, linear amplification resulted with the primers having melting temperatures<60° C. during the first 20 cycles of the "1$^{st}$ Ct" iteration. Touchdown PCR may enable single-tube applications with a minimum of optimization of melting temperatures between the two primers.

TABLE 3

Linear or Exponential amplification

| F T$_m$ | 1$^{st}$ Ct | 2$^{nd}$ Ct | dCt | Lin/Exp |
|---|---|---|---|---|
| 54.9° C. | 28.38 | 31.63 | 3.25 | Linear |
| 57.2° C. | 28.57 | 31.35 | 2.78 | Linear |
| 58.2° C. | 27.97 | 31.50 | 3.53 | Linear |
| 63.0° C. | 23.79 | 31.45 | 7.66 | Mixed |
| 66.4° C. | 21.94 | 31.26 | 9.32 | Mixed |
| 67.0° C. | 18.57 | 31.57 | 13.00 | Exponential |
| 68.5° C. | 15.79 | 31.49 | 15.70 | Exponential |
| 70.0° C. | 19.11 | 28.89 | 9.78 | Exponential |

TABLE 4

Exemplary adapter sequences

| SEQ ID NO | Top Strand* (5'-3') | SEQ ID NO | Bottom Strand* (5'-3') | Universal Amplification Primer | Barcode Domain | Ligation |
|---|---|---|---|---|---|---|
| 1 | ACACTCTTTCCCTACACGACGCTCTTCCGATCT | 4 | pGATCGGAAGAGCp | 1 | none | T/A |
| 1 | ACACTCTTTCCCTACACGACGCTCTTCCGATCT | 3 | pGATCGGAAGAGp | 1 | none | T/A |
| 1 | ACACTCTTTCCCTACACGACGCTCTTCCGATCT | 2 | pGATCGGAAGAp | 1 | none | T/A |
| 1 | ACACTCTTTCCCTACACGACGCTCTTCCGATCT | — | pGATCGGAAGp | 1 | none | T/A |
| 1 | ACACTCTTTCCCTACACGACGCTCTTCCGATCT | — | pGATCGGAAp | 1 | none | T/A |
| 1 | ACACTCTTTCCCTACACGACGCTCTTCCGATCT | 4 | pGATCGGAAGAGCh | 1 | none | T/A |
| 1 | ACACTCTTTCCCTACACGACGCTCTTCCGATCT | 3 | pGATCGGAAGAGh | 1 | none | T/A |
| 1 | ACACTCTTTCCCTACACGACGCTCTTCCGATCT | 2 | pGATCGGAAGAh | 1 | none | T/A |
| 1 | ACACTCTTTCCCTACACGACGCTCTTCCGATCT | — | pGATCGGAAGh | 1 | none | T/A |
| 1 | ACACTCTTTCCCTACACGACGCTCTTCCGATCT | — | pGATCGGAAh | 1 | none | T/A |
| 1 | ACACTCTTTCCCTACACGACGCTCTTCCGATCT | 5 | pGATCGGAAGAGCH | 1 | none | T/A |
| 1 | ACACTCTTTCCCTACACGACGCTCTTCCGATCT | 6 | pGATCGGAAGAGD | 1 | none | T/A |
| 1 | ACACTCTTTCCCTACACGACGCTCTTCCGATCT | 7 | pGATCGGAAGAH | 1 | none | T/A |
| 1 | ACACTCTTTCCCTACACGACGCTCTTCCGATCT | 8 | pGATCGGAAGB | 1 | none | T/A |
| 1 | ACACTCTTTCCCTACACGACGCTCTTCCGATCT | — | pGATCGGAAH | 1 | none | T/A |
| 1 | ACACTCTTTCCCTACACGACGCTCTTCCGATCT | 9 | pGATCGGAAGAGCHV | 1 | none | T/A |
| 1 | ACACTCTTTCCCTACACGACGCTCTTCCGATCT | 10 | pGATCGGAAGAGDH | 1 | none | T/A |
| 1 | ACACTCTTTCCCTACACGACGCTCTTCCGATCT | 11 | pGATCGGAAGAHD | 1 | none | T/A |
| 1 | ACACTCTTTCCCTACACGACGCTCTTCCGATCT | 12 | pGATCGGAAGBH | 1 | none | T/A |
| 1 | ACACTCTTTCCCTACACGACGCTCTTCCGATCT | 13 | pGATCGGAAHB | 1 | none | T/A |
| 1 | ACACTCTTTCCCTACACGACGCTCTTCCGATCT | 14 | pGATCGGAAGAGCHnN | 1 | none | T/A |
| 1 | ACACTCTTTCCCTACACGACGCTCTTCCGATCT | 15 | pGATCGGAAGAGDnN | 1 | none | T/A |
| 1 | ACACTCTTTCCCTACACGACGCTCTTCCGATCT | 16 | pGATCGGAAGAHnN | 1 | none | T/A |
| 1 | ACACTCTTTCCCTACACGACGCTCTTCCGATCT | 17 | pGATCGGAAGBnN | 1 | none | T/A |
| 1 | ACACTCTTTCCCTACACGACGCTCTTCCGATCT | 18 | pGATCGGAAHnN | 1 | none | T/A |
| 19 | ACACTCTTTCCCTACACGACGCTCTTCCGATCNNNNNNNNT | 20 | pN'N'N'N'N'N'N'N'GATCGGAAGAGCp | 2 | 8 base | T/A |
| 19 | ACACTCTTTCCCTACACGACGCTCTTCCGATCNNNNNNNNT | 21 | pN'N'N'N'N'N'N'N'GATCGGAAGAGp | 2 | 8 base | T/A |
| 19 | ACACTCTTTCCCTACACGACGCTCTTCCGATCNNNNNNNNT | 22 | pN'N'N'N'N'N'N'N'GATCGGAAGAp | 2 | 8 base | T/A |
| 19 | ACACTCTTTCCCTACACGACGCTCTTCCGATCNNNNNNNNT | 23 | pN'N'N'N'N'N'N'N'GATCGGAAGp | 2 | 8 base | T/A |
| 19 | ACACTCTTTCCCTACACGACGCTCTTCCGATCNNNNNNNNT | 24 | pN'N'N'N'N'N'N'N'GATCGGAAp | 2 | 8 base | T/A |
| 19 | ACACTCTTTCCCTACACGACGCTCTTCCGATCNNNNNNNNT | 20 | pN'N'N'N'N'N'N'N'GATCGGAAGAGCh | 2 | 8 base | T/A |
| 19 | ACACTCTTTCCCTACACGACGCTCTTCCGATCNNNNNNNNT | 21 | pN'N'N'N'N'N'N'N'GATCGGAAGAGh | 2 | 8 base | T/A |
| 19 | ACACTCTTTCCCTACACGACGCTCTTCCGATCNNNNNNNNT | 22 | pN'N'N'N'N'N'N'N'GATCGGAAGAh | 2 | 8 base | T/A |
| 19 | ACACTCTTTCCCTACACGACGCTCTTCCGATCNNNNNNNNT | 23 | pN'N'N'N'N'N'N'N'GATCGGAAGh | 2 | 8 base | T/A |

TABLE 4-continued

Exemplary adapter sequences

| SEQ ID NO | Top Strand* (5'-3') | SEQ ID NO | Bottom Strand* (5'-3') | Universal Amplification Primer | Barcode Domain | Ligation |
|---|---|---|---|---|---|---|
| 19 | ACACTCTTTCCCTACACGACGCTCTTCCGATCNNNNNNNT | 24 | pN'N'N'N'N'N'N'N'GATCGGAAh | 2 | 8 base | T/A |
| 19 | ACACTCTTTCCCTACACGACGCTCTTCCGATCNNNNNNNT | 25 | pN'N'N'N'N'N'N'N'GATCGGAAGAGCH | 2 | 8 base | T/A |
| 19 | ACACTCTTTCCCTACACGACGCTCTTCCGATCNNNNNNNT | 26 | pN'N'N'N'N'N'N'N'GATCGGAAGAGD | 2 | 8 base | T/A |
| 19 | ACACTCTTTCCCTACACGACGCTCTTCCGATCNNNNNNNT | 27 | pN'N'N'N'N'N'N'N'GATCGGAAGAH | 2 | 8 base | T/A |
| 19 | ACACTCTTTCCCTACACGACGCTCTTCCGATCNNNNNNNT | 28 | pN'N'N'N'N'N'N'N'GATCGGAAGB | 2 | 8 base | T/A |
| 19 | ACACTCTTTCCCTACACGACGCTCTTCCGATCNNNNNNNT | 29 | pN'N'N'N'N'N'N'N'GATCGGAAH | 2 | 8 base | T/A |
| 19 | ACACTCTTTCCCTACACGACGCTCTTCCGATCNNNNNNNT | 30 | pN'N'N'N'N'N'N'N'GATCGGAAGAGCHV | 2 | 8 base | T/A |
| 19 | ACACTCTTTCCCTACACGACGCTCTTCCGATCNNNNNNNT | 31 | pN'N'N'N'N'N'N'N'GATCGGAAGAGDH | 2 | 8 base | T/A |
| 19 | ACACTCTTTCCCTACACGACGCTCTTCCGATCNNNNNNNT | 32 | pN'N'N'N'N'N'N'N'GATCGGAAGAHD | 2 | 8 base | T/A |
| 19 | ACACTCTTTCCCTACACGACGCTCTTCCGATCNNNNNNNT | 33 | pN'N'N'N'N'N'N'N'GATCGGAAGBH | 2 | 8 base | T/A |
| 19 | ACACTCTTTCCCTACACGACGCTCTTCCGATCNNNNNNNT | 34 | pN'N'N'N'N'N'N'N'GATCGGAAHB | 2 | 8 base | T/A |
| 19 | ACACTCTTTCCCTACACGACGCTCTTCCGATCNNNNNNNT | 35 | pN'N'N'N'N'N'N'N'GATCGGAAGAGCHnN | 2 | 8 base | T/A |
| 19 | ACACTCTTTCCCTACACGACGCTCTTCCGATCNNNNNNNT | 36 | pN'N'N'N'N'N'N'N'GATCGGAAGAGDnN | 2 | 8 base | T/A |
| 19 | ACACTCTTTCCCTACACGACGCTCTTCCGATCNNNNNNNT | 37 | pN'N'N'N'N'N'N'N'GATCGGAAGAHnN | 2 | 8 base | T/A |
| 19 | ACACTCTTTCCCTACACGACGCTCTTCCGATCNNNNNNNT | 38 | pN'N'N'N'N'N'N'N'GATCGGAAGBnN | 2 | 8 base | T/A |
| 19 | ACACTCTTTCCCTACACGACGCTCTTCCGATCNNNNNNNT | 39 | pN'N'N'N'N'N'N'N'GATCGGAAHnN | 2 | 8 base | T/A |
| 40 | CCATCTCATCCCTGCGTGTCTCCGACTCAG | 41 | pCTGAGTCGGAGACACGp | 3 | none | Blunt |
| 40 | CCATCTCATCCCTGCGTGTCTCCGACTCAG | 42 | pCTGAGTCGGAGACACp | 3 | none | Blunt |
| 40 | CCATCTCATCCCTGCGTGTCTCCGACTCAG | 43 | pCTGAGTCGGAGACAp | 3 | none | Blunt |
| 40 | CCATCTCATCCCTGCGTGTCTCCGACTCAG | 44 | pCTGAGTCGGAGACp | 3 | none | Blunt |
| 40 | CCATCTCATCCCTGCGTGTCTCCGACTCAG | 45 | pCTGAGTCGGAGAp | 3 | none | Blunt |
| 40 | CCATCTCATCCCTGCGTGTCTCCGACTCAG | 46 | pCTGAGTCGGAGp | 3 | none | Blunt |
| 40 | CCATCTCATCCCTGCGTGTCTCCGACTCAG | 47 | pCTGAGTCGGAp | 3 | none | Blunt |
| 40 | CCATCTCATCCCTGCGTGTCTCCGACTCAG | — | pCTGAGTCGGp | 3 | none | Blunt |
| 40 | CCATCTCATCCCTGCGTGTCTCCGACTCAG | — | pCTGAGTCGp | 3 | none | Blunt |
| 40 | CCATCTCATCCCTGCGTGTCTCCGACTCAG | 41 | pCTGAGTCGGAGACACGh | 3 | none | Blunt |
| 40 | CCATCTCATCCCTGCGTGTCTCCGACTCAG | 42 | pCTGAGTCGGAGACACh | 3 | none | Blunt |
| 40 | CCATCTCATCCCTGCGTGTCTCCGACTCAG | 43 | pCTGAGTCGGAGACAh | 3 | none | Blunt |
| 40 | CCATCTCATCCCTGCGTGTCTCCGACTCAG | 44 | pCTGAGTCGGAGACh | 3 | none | Blunt |
| 40 | CCATCTCATCCCTGCGTGTCTCCGACTCAG | 45 | pCTGAGTCGGAGAh | 3 | none | Blunt |
| 40 | CCATCTCATCCCTGCGTGTCTCCGACTCAG | 46 | pCTGAGTCGGAGh | 3 | none | Blunt |
| 40 | CCATCTCATCCCTGCGTGTCTCCGACTCAG | 47 | pCTGAGTCGGAh | 3 | none | Blunt |
| 40 | CCATCTCATCCCTGCGTGTCTCCGACTCAG | — | pCTGAGTCGGh | 3 | none | Blunt |
| 40 | CCATCTCATCCCTGCGTGTCTCCGACTCAG | — | pCTGAGTCGh | 3 | none | Blunt |
| 40 | CCATCTCATCCCTGCGTGTCTCCGACTCAG | 48 | pCTGAGTCGGAGACACGD | 3 | none | Blunt |
| 40 | CCATCTCATCCCTGCGTGTCTCCGACTCAG | 49 | pCTGAGTCGGAGACACH | 3 | none | Blunt |
| 40 | CCATCTCATCCCTGCGTGTCTCCGACTCAG | 50 | pCTGAGTCGGAGACAD | 3 | none | Blunt |
| 40 | CCATCTCATCCCTGCGTGTCTCCGACTCAG | 51 | pCTGAGTCGGAGACB | 3 | none | Blunt |
| 40 | CCATCTCATCCCTGCGTGTCTCCGACTCAG | 52 | pCTGAGTCGGAGAD | 3 | none | Blunt |
| 40 | CCATCTCATCCCTGCGTGTCTCCGACTCAG | 53 | pCTGAGTCGGAGB | 3 | none | Blunt |
| 40 | CCATCTCATCCCTGCGTGTCTCCGACTCAG | 54 | pCTGAGTCGGAH | 3 | none | Blunt |
| 40 | CCATCTCATCCCTGCGTGTCTCCGACTCAG | 55 | pCTGAGTCGGB | 3 | none | Blunt |
| 40 | CCATCTCATCCCTGCGTGTCTCCGACTCAG | — | pCTGAGTCGH | 3 | none | Blunt |
| 40 | CCATCTCATCCCTGCGTGTCTCCGACTCAG | 56 | pCTGAGTCGGAGACACGDB | 3 | none | Blunt |
| 40 | CCATCTCATCCCTGCGTGTCTCCGACTCAG | 57 | pCTGAGTCGGAGACACHD | 3 | none | Blunt |
| 40 | CCATCTCATCCCTGCGTGTCTCCGACTCAG | 58 | pCTGAGTCGGAGACADH | 3 | none | Blunt |
| 40 | CCATCTCATCCCTGCGTGTCTCCGACTCAG | 59 | pCTGAGTCGGAGACBD | 3 | none | Blunt |
| 40 | CCATCTCATCCCTGCGTGTCTCCGACTCAG | 60 | pCTGAGTCGGAGADB | 3 | none | Blunt |
| 40 | CCATCTCATCCCTGCGTGTCTCCGACTCAG | 61 | pCTGAGTCGGAGBD | 3 | none | Blunt |
| 40 | CCATCTCATCCCTGCGTGTCTCCGACTCAG | 62 | pCTGAGTCGGAHB | 3 | none | Blunt |
| 40 | CCATCTCATCCCTGCGTGTCTCCGACTCAG | 63 | pCTGAGTCGGBH | 3 | none | Blunt |
| 40 | CCATCTCATCCCTGCGTGTCTCCGACTCAG | 64 | pCTGAGTCGHB | 3 | none | Blunt |
| 40 | CCATCTCATCCCTGCGTGTCTCCGACTCAG | 65 | pCTGAGTCGGAGACACGDnN | 3 | none | Blunt |
| 40 | CCATCTCATCCCTGCGTGTCTCCGACTCAG | 66 | pCTGAGTCGGAGACACHnN | 3 | none | Blunt |
| 40 | CCATCTCATCCCTGCGTGTCTCCGACTCAG | 67 | pCTGAGTCGGAGACADnN | 3 | none | Blunt |
| 40 | CCATCTCATCCCTGCGTGTCTCCGACTCAG | 68 | pCTGAGTCGGAGACBnN | 3 | none | Blunt |
| 40 | CCATCTCATCCCTGCGTGTCTCCGACTCAG | 69 | pCTGAGTCGGAGADnN | 3 | none | Blunt |
| 40 | CCATCTCATCCCTGCGTGTCTCCGACTCAG | 70 | pCTGAGTCGGAGBnN | 3 | none | Blunt |

TABLE 4-continued

Exemplary adapter sequences

| SEQ ID NO | Top Strand* (5'-3') | SEQ ID NO | Bottom Strand* (5'-3') | Universal Amplification Primer | Barcode Domain | Ligation |
|---|---|---|---|---|---|---|
| 40 | CCATCTCATCCCTGCGTGTCTCCGACTCAG | 71 | pCTGAGTCGGAHnN | 3 | none | Blunt |
| 40 | CCATCTCATCCCTGCGTGTCTCCGACTCAG | 72 | pCTGAGTCGGBnN | 3 | none | Blunt |
| 40 | CCATCTCATCCCTGCGTGTCTCCGACTCAG | 73 | pCTGAGTCGHnN | 3 | none | Blunt |
| 74 | CCATCTCATCCCTGCGTGTCTCCGACTCAGT | 41 | pCTGAGTCGGAGACACGp | 3 | none | T/A |
| 74 | CCATCTCATCCCTGCGTGTCTCCGACTCAGT | 42 | pCTGAGTCGGAGACACp | 3 | none | T/A |
| 74 | CCATCTCATCCCTGCGTGTCTCCGACTCAGT | 43 | pCTGAGTCGGAGACAp | 3 | none | T/A |
| 74 | CCATCTCATCCCTGCGTGTCTCCGACTCAGT | 44 | pCTGAGTCGGAGACp | 3 | none | T/A |
| 74 | CCATCTCATCCCTGCGTGTCTCCGACTCAGT | 45 | pCTGAGTCGGAGAp | 3 | none | T/A |
| 74 | CCATCTCATCCCTGCGTGTCTCCGACTCAGT | 46 | pCTGAGTCGGAGp | 3 | none | T/A |
| 74 | CCATCTCATCCCTGCGTGTCTCCGACTCAGT | 47 | pCTGAGTCGGAp | 3 | none | T/A |
| 74 | CCATCTCATCCCTGCGTGTCTCCGACTCAGT | — | pCTGAGTCGGp | 3 | none | T/A |
| 74 | CCATCTCATCCCTGCGTGTCTCCGACTCAGT | — | pCTGAGTCGp | 3 | none | T/A |
| 74 | CCATCTCATCCCTGCGTGTCTCCGACTCAGT | 41 | pCTGAGTCGGAGACACGh | 3 | none | T/A |
| 74 | CCATCTCATCCCTGCGTGTCTCCGACTCAGT | 42 | pCTGAGTCGGAGACACh | 3 | none | T/A |
| 74 | CCATCTCATCCCTGCGTGTCTCCGACTCAGT | 43 | pCTGAGTCGGAGACAh | 3 | none | T/A |
| 74 | CCATCTCATCCCTGCGTGTCTCCGACTCAGT | 44 | pCTGAGTCGGAGACh | 3 | none | T/A |
| 74 | CCATCTCATCCCTGCGTGTCTCCGACTCAGT | 45 | pCTGAGTCGGAGAh | 3 | none | T/A |
| 74 | CCATCTCATCCCTGCGTGTCTCCGACTCAGT | 46 | pCTGAGTCGGAGh | 3 | none | T/A |
| 74 | CCATCTCATCCCTGCGTGTCTCCGACTCAGT | 47 | pCTGAGTCGGAh | 3 | none | T/A |
| 74 | CCATCTCATCCCTGCGTGTCTCCGACTCAGT | — | pCTGAGTCGGh | 3 | none | T/A |
| 74 | CCATCTCATCCCTGCGTGTCTCCGACTCAGT | — | pCTGAGTCGh | 3 | none | T/A |
| 74 | CCATCTCATCCCTGCGTGTCTCCGACTCAGT | 48 | pCTGAGTCGGAGACACGD | 3 | none | T/A |
| 74 | CCATCTCATCCCTGCGTGTCTCCGACTCAGT | 49 | pCTGAGTCGGAGACACH | 3 | none | T/A |
| 74 | CCATCTCATCCCTGCGTGTCTCCGACTCAGT | 50 | pCTGAGTCGGAGACAD | 3 | none | T/A |
| 74 | CCATCTCATCCCTGCGTGTCTCCGACTCAGT | 51 | pCTGAGTCGGAGACB | 3 | none | T/A |
| 74 | CCATCTCATCCCTGCGTGTCTCCGACTCAGT | 52 | pCTGAGTCGGAGAD | 3 | none | T/A |
| 74 | CCATCTCATCCCTGCGTGTCTCCGACTCAGT | 53 | pCTGAGTCGGAGB | 3 | none | T/A |
| 74 | CCATCTCATCCCTGCGTGTCTCCGACTCAGT | 54 | pCTGAGTCGGAH | 3 | none | T/A |
| 74 | CCATCTCATCCCTGCGTGTCTCCGACTCAGT | 55 | pCTGAGTCGGB | 3 | none | T/A |
| 74 | CCATCTCATCCCTGCGTGTCTCCGACTCAGT | — | pCTGAGTCGH | 3 | none | T/A |
| 74 | CCATCTCATCCCTGCGTGTCTCCGACTCAGT | 56 | pCTGAGTCGGAGACACGDB | 3 | none | T/A |
| 74 | CCATCTCATCCCTGCGTGTCTCCGACTCAGT | 57 | pCTGAGTCGGAGACACHD | 3 | none | T/A |
| 74 | CCATCTCATCCCTGCGTGTCTCCGACTCAGT | 58 | pCTGAGTCGGAGACADH | 3 | none | T/A |
| 74 | CCATCTCATCCCTGCGTGTCTCCGACTCAGT | 59 | pCTGAGTCGGAGACBD | 3 | none | T/A |
| 74 | CCATCTCATCCCTGCGTGTCTCCGACTCAGT | 60 | pCTGAGTCGGAGADB | 3 | none | T/A |
| 74 | CCATCTCATCCCTGCGTGTCTCCGACTCAGT | 61 | pCTGAGTCGGAGBD | 3 | none | T/A |
| 74 | CCATCTCATCCCTGCGTGTCTCCGACTCAGT | 62 | pCTGAGTCGGAHB | 3 | none | T/A |
| 74 | CCATCTCATCCCTGCGTGTCTCCGACTCAGT | 63 | pCTGAGTCGGBH | 3 | none | T/A |
| 74 | CCATCTCATCCCTGCGTGTCTCCGACTCAGT | 64 | pCTGAGTCGHB | 3 | none | T/A |
| 74 | CCATCTCATCCCTGCGTGTCTCCGACTCAGT | 65 | pCTGAGTCGGAGACACGDnN | 3 | none | T/A |
| 74 | CCATCTCATCCCTGCGTGTCTCCGACTCAGT | 66 | pCTGAGTCGGAGACACHnN | 3 | none | T/A |
| 74 | CCATCTCATCCCTGCGTGTCTCCGACTCAGT | 67 | pCTGAGTCGGAGACADnN | 3 | none | T/A |
| 74 | CCATCTCATCCCTGCGTGTCTCCGACTCAGT | 68 | pCTGAGTCGGAGACBnN | 3 | none | T/A |
| 74 | CCATCTCATCCCTGCGTGTCTCCGACTCAGT | 69 | pCTGAGTCGGAGADnN | 3 | none | T/A |
| 74 | CCATCTCATCCCTGCGTGTCTCCGACTCAGT | 70 | pCTGAGTCGGAGBnN | 3 | none | T/A |
| 74 | CCATCTCATCCCTGCGTGTCTCCGACTCAGT | 71 | pCTGAGTCGGAHnN | 3 | none | T/A |
| 74 | CCATCTCATCCCTGCGTGTCTCCGACTCAGT | 72 | pCTGAGTCGGBnN | 3 | none | T/A |
| 74 | CCATCTCATCCCTGCGTGTCTCCGACTCAGT | 73 | pCTGAGTCGHnN | 3 | none | T/A |
| 75 | CCATCTCATCCCTGCGTGTCTCCGACTCAGNNNNNNNN | 76 | pN'N'N'N'N'N'N'NCTGAGTCGGAGACACGp | 3 | 8 base | Blunt |
| 75 | CCATCTCATCCCTGCGTGTCTCCGACTCAGNNNNNNNN | 77 | pN'N'N'N'N'N'N'NCTGAGTCGGAGACACp | 3 | 8 base | Blunt |
| 75 | CCATCTCATCCCTGCGTGTCTCCGACTCAGNNNNNNNN | 78 | pN'N'N'N'N'N'N'NCTGAGTCGGAGACAp | 3 | 8 base | Blunt |
| 75 | CCATCTCATCCCTGCGTGTCTCCGACTCAGNNNNNNNN | 79 | pN'N'N'N'N'N'N'NCTGAGTCGGAGACp | 3 | 8 base | Blunt |
| 75 | CCATCTCATCCCTGCGTGTCTCCGACTCAGNNNNNNNN | 80 | pN'N'N'N'N'N'N'NCTGAGTCGGAGAp | 3 | 8 base | Blunt |
| 75 | CCATCTCATCCCTGCGTGTCTCCGACTCAGNNNNNNNN | 81 | pN'N'N'N'N'N'N'NCTGAGTCGGAGp | 3 | 8 base | Blunt |
| 75 | CCATCTCATCCCTGCGTGTCTCCGACTCAGNNNNNNNN | 82 | pN'N'N'N'N'N'N'NCTGAGTCGGAp | 3 | 8 base | Blunt |
| 75 | CCATCTCATCCCTGCGTGTCTCCGACTCAGNNNNNNNN | 83 | pN'N'N'N'N'N'N'NCTGAGTCGGp | 3 | 8 base | Blunt |
| 75 | CCATCTCATCCCTGCGTGTCTCCGACTCAGNNNNNNNN | 84 | pN'N'N'N'N'N'N'NCTGAGTCGp | 3 | 8 base | Blunt |
| 75 | CCATCTCATCCCTGCGTGTCTCCGACTCAGNNNNNNNN | 76 | pN'N'N'N'N'N'N'NCTGAGTCGGAGACACGh | 3 | 8 base | Blunt |
| 75 | CCATCTCATCCCTGCGTGTCTCCGACTCAGNNNNNNNN | 77 | pN'N'N'N'N'N'N'NCTGAGTCGGAGACACh | 3 | 8 base | Blunt |
| 75 | CCATCTCATCCCTGCGTGTCTCCGACTCAGNNNNNNNN | 78 | pN'N'N'N'N'N'N'NCTGAGTCGGAGACAh | 3 | 8 base | Blunt |
| 75 | CCATCTCATCCCTGCGTGTCTCCGACTCAGNNNNNNNN | 79 | pN'N'N'N'N'N'N'NCTGAGTCGGAGACh | 3 | 8 base | Blunt |

TABLE 4-continued

Exemplary adapter sequences

| SEQ ID NO | Top Strand* (5'-3') | SEQ ID NO | Bottom Strand* (5'-3') | Universal Amplification Primer | Barcode Domain | Ligation |
|---|---|---|---|---|---|---|
| 75 | CCATCTCATCCCTGCGTGTCTCCGACTCAGNNNNNNNN | 80 | pN'N'N'N'N'N'N'NCTGAGTCGGAGAh | 3 | 8 base | Blunt |
| 75 | CCATCTCATCCCTGCGTGTCTCCGACTCAGNNNNNNNN | 81 | pN'N'N'N'N'N'N'NCTGAGTCGGAGh | 3 | 8 base | Blunt |
| 75 | CCATCTCATCCCTGCGTGTCTCCGACTCAGNNNNNNNN | 82 | pN'N'N'N'N'N'N'NCTGAGTCGGAh | 3 | 8 base | Blunt |
| 75 | CCATCTCATCCCTGCGTGTCTCCGACTCAGNNNNNNNN | 83 | pN'N'N'N'N'N'N'NCTGAGTCGGh | 3 | 8 base | Blunt |
| 75 | CCATCTCATCCCTGCGTGTCTCCGACTCAGNNNNNNNN | 84 | pN'N'N'N'N'N'N'NCTGAGTCGh | 3 | 8 base | Blunt |
| 75 | CCATCTCATCCCTGCGTGTCTCCGACTCAGNNNNNNNN | 85 | pN'N'N'N'N'N'N'NCTGAGTCGGAGACACGD | 3 | 8 base | Blunt |
| 75 | CCATCTCATCCCTGCGTGTCTCCGACTCAGNNNNNNNN | 86 | pN'N'N'N'N'N'N'NCTGAGTCGGAGACACH | 3 | 8 base | Blunt |
| 75 | CCATCTCATCCCTGCGTGTCTCCGACTCAGNNNNNNNN | 87 | pN'N'N'N'N'N'N'NCTGAGTCGGAGACAD | 3 | 8 base | Blunt |
| 75 | CCATCTCATCCCTGCGTGTCTCCGACTCAGNNNNNNNN | 88 | pN'N'N'N'N'N'N'NCTGAGTCGGAGACB | 3 | 8 base | Blunt |
| 75 | CCATCTCATCCCTGCGTGTCTCCGACTCAGNNNNNNNN | 89 | pN'N'N'N'N'N'N'NCTGAGTCGGAGAD | 3 | 8 base | Blunt |
| 75 | CCATCTCATCCCTGCGTGTCTCCGACTCAGNNNNNNNN | 90 | pN'N'N'N'N'N'N'NCTGAGTCGGAGB | 3 | 8 base | Blunt |
| 75 | CCATCTCATCCCTGCGTGTCTCCGACTCAGNNNNNNNN | 91 | pN'N'N'N'N'N'N'NCTGAGTCGGAH | 3 | 8 base | Blunt |
| 75 | CCATCTCATCCCTGCGTGTCTCCGACTCAGNNNNNNNN | 92 | pN'N'N'N'N'N'N'NCTGAGTCGGB | 3 | 8 base | Blunt |
| 75 | CCATCTCATCCCTGCGTGTCTCCGACTCAGNNNNNNNN | 93 | pN'N'N'N'N'N'N'NCTGAGTCGH | 3 | 8 base | Blunt |
| 75 | CCATCTCATCCCTGCGTGTCTCCGACTCAGNNNNNNNN | 94 | pN'N'N'N'N'N'N'NCTGAGTCGGAGACACGDB | 3 | 8 base | Blunt |
| 75 | CCATCTCATCCCTGCGTGTCTCCGACTCAGNNNNNNNN | 95 | pN'N'N'N'N'N'N'NCTGAGTCGGAGACACHD | 3 | 8 base | Blunt |
| 75 | CCATCTCATCCCTGCGTGTCTCCGACTCAGNNNNNNNN | 96 | pN'N'N'N'N'N'N'NCTGAGTCGGAGACADH | 3 | 8 base | Blunt |
| 75 | CCATCTCATCCCTGCGTGTCTCCGACTCAGNNNNNNNN | 97 | pN'N'N'N'N'N'N'NCTGAGTCGGAGACBD | 3 | 8 base | Blunt |
| 75 | CCATCTCATCCCTGCGTGTCTCCGACTCAGNNNNNNNN | 98 | pN'N'N'N'N'N'N'NCTGAGTCGGAGADB | 3 | 8 base | Blunt |
| 75 | CCATCTCATCCCTGCGTGTCTCCGACTCAGNNNNNNNN | 99 | pN'N'N'N'N'N'N'NCTGAGTCGGAGBD | 3 | 8 base | Blunt |
| 75 | CCATCTCATCCCTGCGTGTCTCCGACTCAGNNNNNNNN | 100 | pN'N'N'N'N'N'N'NCTGAGTCGGAHB | 3 | 8 base | Blunt |
| 75 | CCATCTCATCCCTGCGTGTCTCCGACTCAGNNNNNNNN | 101 | pN'N'N'N'N'N'N'NCTGAGTCGGBH | 3 | 8 base | Blunt |
| 75 | CCATCTCATCCCTGCGTGTCTCCGACTCAGNNNNNNNN | 102 | pN'N'N'N'N'N'N'NCTGAGTCGHB | 3 | 8 base | Blunt |
| 75 | CCATCTCATCCCTGCGTGTCTCCGACTCAGNNNNNNNN | 103 | pN'N'N'N'N'N'N'NCTGAGTCGGAGACACGDnN | 3 | 8 base | Blunt |
| 75 | CCATCTCATCCCTGCGTGTCTCCGACTCAGNNNNNNNN | 104 | pN'N'N'N'N'N'N'NCTGAGTCGGAGACACHnN | 3 | 8 base | Blunt |
| 75 | CCATCTCATCCCTGCGTGTCTCCGACTCAGNNNNNNNN | 105 | pN'N'N'N'N'N'N'NCTGAGTCGGAGACADnN | 3 | 8 base | Blunt |
| 75 | CCATCTCATCCCTGCGTGTCTCCGACTCAGNNNNNNNN | 106 | pN'N'N'N'N'N'N'NCTGAGTCGGAGACBnN | 3 | 8 base | Blunt |
| 75 | CCATCTCATCCCTGCGTGTCTCCGACTCAGNNNNNNNN | 107 | pN'N'N'N'N'N'N'NCTGAGTCGGAGADnN | 3 | 8 base | Blunt |
| 75 | CCATCTCATCCCTGCGTGTCTCCGACTCAGNNNNNNNN | 108 | pN'N'N'N'N'N'N'NCTGAGTCGGAGBnN | 3 | 8 base | Blunt |
| 75 | CCATCTCATCCCTGCGTGTCTCCGACTCAGNNNNNNNN | 109 | pN'N'N'N'N'N'N'NCTGAGTCGGAHnN | 3 | 8 base | Blunt |
| 75 | CCATCTCATCCCTGCGTGTCTCCGACTCAGNNNNNNNN | 110 | pN'N'N'N'N'N'N'NCTGAGTCGGBnN | 3 | 8 base | Blunt |
| 75 | CCATCTCATCCCTGCGTGTCTCCGACTCAGNNNNNNNN | 111 | pN'N'N'N'N'N'N'NCTGAGTCGHnN | 3 | 8 base | Blunt |
| 112 | CCATCTCATCCCTGCGTGTCTCCGACTCAGNNNNNNNNT | 76 | pN'N'N'N'N'N'N'NCTGAGTCGGAGACACGp | 3 | 8 base | T/A |
| 112 | CCATCTCATCCCTGCGTGTCTCCGACTCAGNNNNNNNNT | 77 | pN'N'N'N'N'N'N'NCTGAGTCGGAGACACp | 3 | 8 base | T/A |
| 112 | CCATCTCATCCCTGCGTGTCTCCGACTCAGNNNNNNNNT | 78 | pN'N'N'N'N'N'N'NCTGAGTCGGAGACAp | 3 | 8 base | T/A |
| 112 | CCATCTCATCCCTGCGTGTCTCCGACTCAGNNNNNNNNT | 79 | pN'N'N'N'N'N'N'NCTGAGTCGGAGACp | 3 | 8 base | T/A |
| 112 | CCATCTCATCCCTGCGTGTCTCCGACTCAGNNNNNNNNT | 80 | pN'N'N'N'N'N'N'NCTGAGTCGGAGAp | 3 | 8 base | T/A |

TABLE 4-continued

Exemplary adapter sequences

| SEQ ID NO | Top Strand* (5'-3') | SEQ ID NO | Bottom Strand* (5'-3') | Universal Amplification Primer | Barcode Domain | Ligation |
|---|---|---|---|---|---|---|
| 112 | CCATCTCATCCCTGCGTGTCTCCGACTCAGNNNNNNNT | 81 | pN'N'N'N'N'N'N'NCTGAGTCGGAGp | 3 | 8 base | T/A |
| 112 | CCATCTCATCCCTGCGTGTCTCCGACTCAGNNNNNNNT | 82 | pN'N'N'N'N'N'N'NCTGAGTCGGAp | 3 | 8 base | T/A |
| 112 | CCATCTCATCCCTGCGTGTCTCCGACTCAGNNNNNNNT | 83 | pN'N'N'N'N'N'N'NCTGAGTCGGp | 3 | 8 base | T/A |
| 112 | CCATCTCATCCCTGCGTGTCTCCGACTCAGNNNNNNNT | 84 | pN'N'N'N'N'N'N'NCTGAGTCGp | 3 | 8 base | T/A |
| 112 | CCATCTCATCCCTGCGTGTCTCCGACTCAGNNNNNNNT | 76 | pN'N'N'N'N'N'N'NCTGAGTCGGAGACACGh | 3 | 8 base | T/A |
| 112 | CCATCTCATCCCTGCGTGTCTCCGACTCAGNNNNNNNT | 77 | pN'N'N'N'N'N'N'NCTGAGTCGGAGACACh | 3 | 8 base | T/A |
| 112 | CCATCTCATCCCTGCGTGTCTCCGACTCAGNNNNNNNT | 78 | pN'N'N'N'N'N'N'NCTGAGTCGGAGACAh | 3 | 8 base | T/A |
| 112 | CCATCTCATCCCTGCGTGTCTCCGACTCAGNNNNNNNT | 79 | pN'N'N'N'N'N'N'NCTGAGTCGGAGACh | 3 | 8 base | T/A |
| 112 | CCATCTCATCCCTGCGTGTCTCCGACTCAGNNNNNNNT | 80 | pN'N'N'N'N'N'N'NCTGAGTCGGAGAh | 3 | 8 base | T/A |
| 112 | CCATCTCATCCCTGCGTGTCTCCGACTCAGNNNNNNNT | 81 | pN'N'N'N'N'N'N'NCTGAGTCGGAGh | 3 | 8 base | T/A |
| 112 | CCATCTCATCCCTGCGTGTCTCCGACTCAGNNNNNNNT | 82 | pN'N'N'N'N'N'N'NCTGAGTCGGAh | 3 | 8 base | T/A |
| 112 | CCATCTCATCCCTGCGTGTCTCCGACTCAGNNNNNNNT | 83 | pN'N'N'N'N'N'N'NCTGAGTCGGh | 3 | 8 base | T/A |
| 112 | CCATCTCATCCCTGCGTGTCTCCGACTCAGNNNNNNNT | 84 | pN'N'N'N'N'N'N'NCTGAGTCGh | 3 | 8 base | T/A |
| 112 | CCATCTCATCCCTGCGTGTCTCCGACTCAGNNNNNNNT | 85 | pN'N'N'N'N'N'N'NCTGAGTCGGAGACACGD | 3 | 8 base | T/A |
| 112 | CCATCTCATCCCTGCGTGTCTCCGACTCAGNNNNNNNT | 86 | pN'N'N'N'N'N'N'NCTGAGTCGGAGACACH | 3 | 8 base | T/A |
| 112 | CCATCTCATCCCTGCGTGTCTCCGACTCAGNNNNNNNT | 87 | pN'N'N'N'N'N'N'NCTGAGTCGGAGACAD | 3 | 8 base | T/A |
| 112 | CCATCTCATCCCTGCGTGTCTCCGACTCAGNNNNNNNT | 88 | pN'N'N'N'N'N'N'NCTGAGTCGGAGACB | 3 | 8 base | T/A |
| 112 | CCATCTCATCCCTGCGTGTCTCCGACTCAGNNNNNNNT | 89 | pN'N'N'N'N'N'N'NCTGAGTCGGAGAD | 3 | 8 base | T/A |
| 112 | CCATCTCATCCCTGCGTGTCTCCGACTCAGNNNNNNNT | 90 | pN'N'N'N'N'N'N'NCTGAGTCGGAGB | 3 | 8 base | T/A |
| 112 | CCATCTCATCCCTGCGTGTCTCCGACTCAGNNNNNNNT | 91 | pN'N'N'N'N'N'N'NCTGAGTCGGAH | 3 | 8 base | T/A |
| 112 | CCATCTCATCCCTGCGTGTCTCCGACTCAGNNNNNNNT | 92 | pN'N'N'N'N'N'N'NCTGAGTCGGB | 3 | 8 base | T/A |
| 112 | CCATCTCATCCCTGCGTGTCTCCGACTCAGNNNNNNNT | 93 | pN'N'N'N'N'N'N'NCTGAGTCGH | 3 | 8 base | T/A |
| 112 | CCATCTCATCCCTGCGTGTCTCCGACTCAGNNNNNNNT | 94 | pN'N'N'N'N'N'N'NCTGAGTCGGAGACACGDB | 3 | 8 base | T/A |
| 112 | CCATCTCATCCCTGCGTGTCTCCGACTCAGNNNNNNNT | 95 | pN'N'N'N'N'N'N'NCTGAGTCGGAGACACHD | 3 | 8 base | T/A |
| 112 | CCATCTCATCCCTGCGTGTCTCCGACTCAGNNNNNNNT | 96 | pN'N'N'N'N'N'N'NCTGAGTCGGAGACADH | 3 | 8 base | T/A |
| 112 | CCATCTCATCCCTGCGTGTCTCCGACTCAGNNNNNNNT | 97 | pN'N'N'N'N'N'N'NCTGAGTCGGAGACBD | 3 | 8 base | T/A |
| 112 | CCATCTCATCCCTGCGTGTCTCCGACTCAGNNNNNNNT | 98 | pN'N'N'N'N'N'N'NCTGAGTCGGAGADB | 3 | 8 base | T/A |
| 112 | CCATCTCATCCCTGCGTGTCTCCGACTCAGNNNNNNNT | 99 | pN'N'N'N'N'N'N'NCTGAGTCGGAGBD | 3 | 8 base | T/A |
| 112 | CCATCTCATCCCTGCGTGTCTCCGACTCAGNNNNNNNT | 100 | pN'N'N'N'N'N'N'NCTGAGTCGGAHB | 3 | 8 base | T/A |
| 112 | CCATCTCATCCCTGCGTGTCTCCGACTCAGNNNNNNNT | 101 | pN'N'N'N'N'N'N'NCTGAGTCGGBH | 3 | 8 base | T/A |
| 112 | CCATCTCATCCCTGCGTGTCTCCGACTCAGNNNNNNNT | 102 | pN'N'N'N'N'N'N'NCTGAGTCGHB | 3 | 8 base | T/A |
| 112 | CCATCTCATCCCTGCGTGTCTCCGACTCAGNNNNNNNT | 103 | pN'N'N'N'N'N'N'NCTGAGTCGGAGACACGDnN | 3 | 8 base | T/A |
| 112 | CCATCTCATCCCTGCGTGTCTCCGACTCAGNNNNNNNT | 104 | pN'N'N'N'N'N'N'NCTGAGTCGGAGACACHnN | 3 | 8 base | T/A |
| 112 | CCATCTCATCCCTGCGTGTCTCCGACTCAGNNNNNNNT | 105 | pN'N'N'N'N'N'N'NCTGAGTCGGAGACADnN | 3 | 8 base | T/A |
| 112 | CCATCTCATCCCTGCGTGTCTCCGACTCAGNNNNNNNT | 106 | pN'N'N'N'N'N'N'NCTGAGTCGGAGACBnN | 3 | 8 base | T/A |
| 112 | CCATCTCATCCCTGCGTGTCTCCGACTCAGNNNNNNNT | 107 | pN'N'N'N'N'N'N'NCTGAGTCGGAGADnN | 3 | 8 base | T/A |
| 112 | CCATCTCATCCCTGCGTGTCTCCGACTCAGNNNNNNNT | 108 | pN'N'N'N'N'N'N'NCTGAGTCGGAGBnN | 3 | 8 base | T/A |

TABLE 4-continued

Exemplary adapter sequences

| SEQ ID NO | Top Strand* (5'-3') | SEQ ID NO | Bottom Strand* (5'-3') | Universal Amplification Primer | Barcode Domain | Ligation |
|---|---|---|---|---|---|---|
| 112 | CCATCTCATCCCTGCGTGTCTCCGACTCAGNNN NNNNNT | 109 | pN'N'N'N'N'N'N'NCTGAGTCG GAHnN | 3 | 8 base | T/A |
| 112 | CCATCTCATCCCTGCGTGTCTCCGACTCAGNNN NNNNNT | 110 | pN'N'N'N'N'N'N'NCTGAGTCG GBnN | 3 | 8 base | T/A |
| 112 | CCATCTCATCCCTGCGTGTCTCCGACTCAGNNN NNNNNT | 111 | pN'N'N'N'N'N'N'NCTGAGTCG HnN | 3 | 8 base | T/A |

*Codes" p =phosphate; h =hydrogen; N = A, C, G or T, B = not A, D = not C, H = not G, V = not T, N' = complement of N, nN = >1 N.
**Universal amplification primer 1 =ACACTCTTTCCCTACACGACGCTCTTCCGATCT (SEQ ID NO: 1)
Universal amplification primer 2 =ACACTCTTTCCCTACACGACGCTCTTCCGATC (SEQ ID NO: 113)
Universal amplification primer 3 =CCATCTCATCCCTGCGTGTCTCCGACTCAG (SEQ ID NO: 40)

Example 6

A blood sample is collected from a patient harboring an as-yet undetected tumor. The frequency of tumor DNA in the patient's blood is dramatically less than that of normal DNA, on the order of 1 cancer genome for every $10^4$ normal genome. Cell free DNA is isolated from a blood sample. The isolated DNA, end-polished, and universal adapter sequences are ligated to the polished fragments. The fragments are amplified by PCR, using a forward primer specific to the universal adapter sequences, and a mix of reverse primers specific to sequences downstream of various known cancer mutations. Based on specific and accurate detection of cancer signature mutations in one or more of these tested sequences, the presence of malignancy cancer is detected at a very early stage.

Example 7

A plant bearing a newly-introduced transgenic trait is crossed with the commercial germ plasm of a commercial seed producer. Polyploid progeny are produced from this cross and cotyledon clippings are collected from the seedlings. gDNA is isolated from each clipping and fragmented. The fragments are end-polished. Universal adapter sequences are ligated to the polished fragments, and PCR is performed using forward primers specific to the universal adapter sequences, and reverse primers specific to trait sequence. Relative prevalence of fragments from each seedling with and without the trait indicates the copy number of the trait allele in each seedling, so that future crosses may be optimized accordingly.

Example 8

Water samples are collected each day over the course of a week from a recreational beach. Microorganisms are filtered from the samples and total DNA is isolated from each filtrate. The DNA is fragmented and the fragments are end-polished. Universal adapter sequences are ligated to the polished fragments. The fragments are analyzed by PCR using forward primers specific for the universal adapter and reverse primers specific to a variety of pathogens. The relative prevalence of each pathogen in each sample is determined based on the number of unique identification sequences in the amplicon pool from each primer pair. In this way, the waxing and waning of different pathogen species frequencies is tracked over time at this beach.

Example 9

Figure 7:
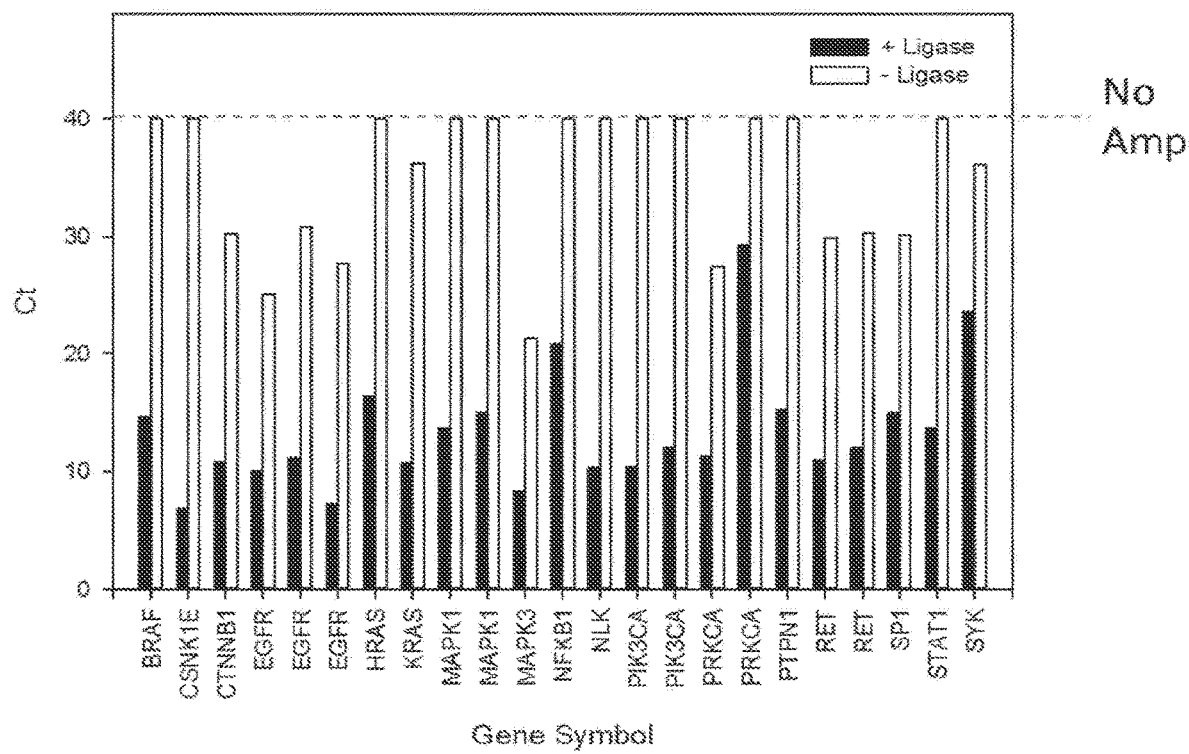
FIG. 7 shows Ct values for the indicated gene targets with or without a ligated adapter sequence (+/− ligase).

Circulating cell free DNA was isolated in 50 µL of elution buffer from 10 ml of human plasma using a circulating nucleic acid isolation kit (e.g., Qiagen). Five µL of the isolated DNA was end repaired and A tailed according to manufacturer's methods using reagents from a commercial next generation sequencing library preparation kit (KAPA Hyper Prep Kit, Kapabiosystems). Adapter ligation (+/− ligase) to the end repaired DNA was performed substituting the adapter composed of ACACTCTTTCCCTA-CACGACGCTCTTCCGATCT (SEQ ID NO:1)+[Phos] GAUCGGAAG[Phos] for recommended Y adapters using ligation components from the Kapa kit. Touchdown qPCRs were performed between universal primer ACACTCTTTCCCTACACGACGCTC (SEQ ID NO:114) and specific primers listed below in Table 5 (0.2 µM universal, 0.2 µM specific, 1×SYBR Green Jumpstart Taq Readimix). Cycling parameters were 20 cycles of 94° C./15 sec, 72° C./15 sec decrease 0.3° C. per cycle, followed by 39 cycles of 94° C./15 sec, 65° C./15 sec, 72° C./15. The results are shown below in Table 5 and FIG. 7. Large delta Cts between + and − ligase reactions indicate amplification between the universal and specific primers.

TABLE 5

Specific Primers

| Gene | Sequence | SEQ ID NO: | +Ligase Ct | −Ligase Ct |
|---|---|---|---|---|
| BRAF | AGTAAAAATAGGTGATTTTGGTCTA | 115 | 14.61 | no amp |
| CSNK1E | CCACTGTCCCTAGATACTTCCA | 116 | 6.92 | no amp |
| CTNNB1 | GCCTCCAGACTTAAAGATGG | 117 | 10.79 | 30.23 |
| EGFR | ACGCTGCGGAGGC | 118 | 10.03 | 25.12 |

TABLE 5-continued

Specific Primers

| Gene | Sequence | SEQ ID NO: | +Ligase Ct | −Ligase Ct |
|---|---|---|---|---|
| EGFR | TTCCGCACCCAGCAG | 119 | 7.25 | 27.72 |
| EGFR | CACCTCCACCGTGCA | 120 | 11.21 | 30.82 |
| HRAS | GGGGACCAGGGGC | 121 | 16.36 | no amp |
| KRAS | GTCAAGGCACTCTTGCC | 122 | 10.66 | 36.27 |
| MAPK1 | GACATGATGAGATCTTCCTGTAT | 123 | 13.73 | no amp |
| MAPK1 | AAGTCACTTCATTAAATTAAGAAGAGTT | 124 | 14.95 | no amp |
| MAPK3 | CCGAGCTTAGCAGCTAGG | 125 | 8.31 | 21.41 |
| NFKB1 | GGAATATTTCTCATTCCCAGATTA | 126 | 20.88 | no amp |
| NLK | GCGCCACAAAGAGACATT | 127 | 10.33 | no amp |
| PIK3CA | ATAGAAAATCTTTCTCCTGCTCA | 128 | 10.38 | no amp |
| PIK3CA | CATTTTTGTTGTCCAGCC | 129 | 11.97 | no amp |
| PRKCA | GCCTTTCCTGCAGCC | 130 | 11.23 | 27.51 |
| PRKCA | ATGTTAATGATCTTTTTCTTTATTTAAAA | 131 | 29.34 | no amp |
| PTPN1 | CTTGAACATCCCCTCAGAC | 132 | 15.3 | no amp |
| RET | GGCCCAGCGTCCA | 133 | 10.96 | 29.94 |
| RET | GTTGAGAACCAGCCCTG | 134 | 11.96 | 30.4 |
| SP1 | CCTTGGGGCAGACCA | 135 | 15.01 | 30.22 |
| STAT1 | GGACATTTATTTGTACCTTCTGTAAT | 136 | 13.65 | no amp |
| SYK | CACCCAGGTAGTTGCG | 137 | 23.63 | 36.11 |

All references, patents, and patent applications referred to in this application are herein incorporated by reference in their entireties. As used in the present disclosure and claims, the singular forms "a," "an," and "the" include plural forms unless the context clearly dictates otherwise. The term "and/or" as used in a phrase such as "A and/or B" herein is intended to include "A and B," "A or B," "A," and "B." While the claimed methods, kits, and compositions have been described and illustrated herein by references to various specific materials, procedures, and examples, it is understood that the invention is not restricted to the particular combinations of material and procedures selected for that purpose. Numerous variations of such details can be implied as will be appreciated by those skilled in the art. It is intended that the specification and examples be considered as exemplary only. The true scope and spirit of the invention is indicated by the following claims.

What is claimed is:

1. A method for copying a sequence of interest, the method comprising
   amplifying a plurality of template polynucleotides, each comprising a randomly fragmented native sequence and a universal adapter sequence on at least one end, the randomly fragmented native sequence comprising the sequence of interest, and the universal adapter sequence comprising 5' to 3' a non-primable adapter priming domain and, optionally, a barcode domain consisting of 1 to 20 nucleotides;
   wherein the universal adapter sequence is located a fixed distance from the 5' end of the sequence of interest, such that the nucleotide sequence between the universal adapter sequence and the sequence of interest defines an identification sequence that is unique to a given template and its progeny amplicons, and wherein the universal adapter sequence has a top strand and a non-extendable bottom strand, wherein the bottom strand is non-complementary to a primer sequence of the top strand; and
   wherein the amplification is primed with a pair of primers comprising a universal primer that is identical to at least 10 bp of the adapter priming domain of the universal adapter sequence and a first reverse primer that is complementary to a region of the native sequence downstream of the sequence of interest.

2. The method of claim 1, wherein the sequence of interest is a mutation, a SNP, or an INDEL.

3. The method of claim 1, further comprising ligating a plurality of universal adapter sequences to a plurality of native sequence polynucleotides to generate the plurality of template polynucleotides.

4. The method of claim 3, further comprising treating the ligation products with a 3' to 5' single-strand specific exonuclease prior to amplifying.

5. The method of claim 1, further comprising amplifying the amplicons with a pair of primers comprising the universal primer and a second reverse primer that is complementary to a sequence upstream of the region complementary to the first reverse primer.

6. The method of claim 5, wherein the second reverse primer comprises a 5' sequencing tag.

7. The method of claim 1, wherein the template polynucleotides comprise fragmented genomic DNA.

8. The method of claim 1, wherein the template polynucleotides comprise cDNA.

9. The method of claim 1, wherein the first reverse primer has a melting temperature that is at least about 5° C., or at least about 10° C. higher than the melting temperature of the universal primer.

10. The method of claim 1, wherein the adapter priming domain is chosen from one or more of SEQ ID NOS: 1, 19, 40, 74, 75, 112, and 113, and wherein each individual template polynucleotide has a probability greater than 95%, greater than 99%, or greater than 99.9% of being molecularly unique just before the initial amplification step.

* * * * *